US008968319B2

(12) United States Patent
Chin et al.

(10) Patent No.: US 8,968,319 B2
(45) Date of Patent: Mar. 3, 2015

(54) METHODS, TOOLS AND DEVICES FOR SPINAL FIXATION

(75) Inventors: Kingsley R. Chin, Wilton Manors, FL (US); Craig Henshaw, Charlestown, MA (US); Matthew Ibarra, Lakewood, CA (US); Jeremy Levinson Crossgrove, Storrs, CT (US)

(73) Assignee: Spinefrontier, Inc, Beverly, MA (US)

( * ) Notice: Subject to any disclaimer, the term of this patent is extended or adjusted under 35 U.S.C. 154(b) by 81 days.

(21) Appl. No.: 13/527,557

(22) Filed: Jun. 19, 2012

(65) Prior Publication Data

US 2012/0323280 A1    Dec. 20, 2012

Related U.S. Application Data

(60) Provisional application No. 61/498,668, filed on Jun. 20, 2011.

(51) Int. Cl.
*A61B 17/88* (2006.01)
*A61B 17/17* (2006.01)
*A61B 17/70* (2006.01)
*A61B 19/00* (2006.01)

(52) U.S. Cl.
CPC ......... *A61B 17/8861* (2013.01); *A61B 17/1757* (2013.01); *A61B 17/7085* (2013.01); *A61B 17/7035* (2013.01); *A61B 2019/307* (2013.01)
USPC ............................. 606/86 A; 606/74; 606/103

(58) Field of Classification Search
USPC .......... 606/86 A, 74, 103, 250–278, 144, 148
See application file for complete search history.

(56) References Cited

U.S. PATENT DOCUMENTS

| 6,146,386 | A | * | 11/2000 | Blackman et al. ............ 606/103 |
| 7,160,300 | B2 | | 1/2007 | Jackson |
| 7,621,918 | B2 | | 11/2009 | Jackson |
| 7,942,878 | B2 | * | 5/2011 | Fernandez ...................... 606/74 |
| 8,092,461 | B2 | * | 1/2012 | Geist et al. .................. 606/86 A |
| 8,267,968 | B2 | * | 9/2012 | Remington et al. .......... 606/264 |
| 8,333,771 | B2 | * | 12/2012 | Geist et al. .................. 606/86 A |
| 8,403,963 | B2 | * | 3/2013 | Garcia-Bengochea et al. ............................. 606/279 |
| 2005/0065517 | A1 | * | 3/2005 | Chin ............................... 606/61 |
| 2005/0192570 | A1 | | 9/2005 | Jackson |
| 2005/0215999 | A1 | | 9/2005 | Birkmeyer et al. |
| 2006/0069391 | A1 | | 3/2006 | Jackson |
| 2006/0111712 | A1 | | 5/2006 | Jackson |
| 2006/0111713 | A1 | | 5/2006 | Jackson |
| 2006/0184178 | A1 | | 8/2006 | Jackson |
| 2006/0293680 | A1 | | 12/2006 | Jackson |
| 2007/0032162 | A1 | | 2/2007 | Jackson |
| 2007/0073294 | A1 | | 3/2007 | Chin et al. |

(Continued)

*Primary Examiner* — Jan Christopher Merene
(74) *Attorney, Agent, or Firm* — AKC Patents LLC; Aliki K. Collins

(57) ABSTRACT

A method for spinal rod insertion includes providing a U-shaped hook tool comprising first and second legs, and inserting the first leg into a first location of a first vertebra and then pushing the hook tool along an arc-shaped path until the first leg exits through a second location of an adjacent second vertebra. Next, providing a spinal stabilization rod and a folded flexible wire comprising first and second open ends at the front end and a closed loop end. The closed loop end is attached to a first end of the spinal stabilization rod and the first and second open ends of the folded flexible wire are inserted into an open end of the second leg of the hook, and the folded flexible wire is threaded through the U-shaped hook and the first and second open ends of the flexible wire exit through an open end of the first leg.

20 Claims, 27 Drawing Sheets

(56) References Cited

U.S. PATENT DOCUMENTS

| | | |
|---|---|---|
| 2007/0233079 A1 | 10/2007 | Fallin et al. |
| 2007/0288026 A1* | 12/2007 | Shluzas .................. 606/73 |
| 2008/0015582 A1 | 1/2008 | DiPoto |
| 2008/0077136 A1 | 3/2008 | Triplett et al. |
| 2008/0082172 A1 | 4/2008 | Jackson |
| 2008/0091213 A1 | 4/2008 | Jackson |
| 2008/0114403 A1 | 5/2008 | Kuester et al. |
| 2008/0288005 A1 | 11/2008 | Jackson |
| 2008/0312704 A1 | 12/2008 | Hestad |
| 2009/0012563 A1* | 1/2009 | Alleyne et al. ............ 606/246 |
| 2009/0099605 A1 | 4/2009 | Fallin et al. |
| 2009/0171391 A1 | 7/2009 | Hutton et al. |
| 2009/0171392 A1 | 7/2009 | Garcia-Bengochea |
| 2009/0198281 A1 | 8/2009 | Rice |
| 2009/0228056 A1 | 9/2009 | Jackson |
| 2009/0318972 A1 | 12/2009 | Jackson |
| 2010/0004696 A1 | 1/2010 | Jackson |
| 2010/0145389 A1 | 6/2010 | Triplett et al. |
| 2010/0249856 A1 | 9/2010 | Iott et al. |
| 2014/0018868 A1* | 1/2014 | Garcia-Bengochea et al. 606/86 A |

* cited by examiner

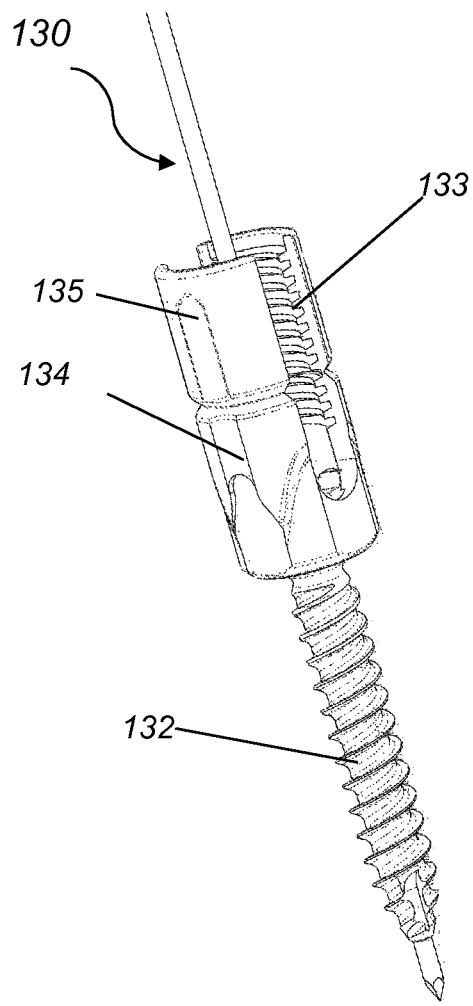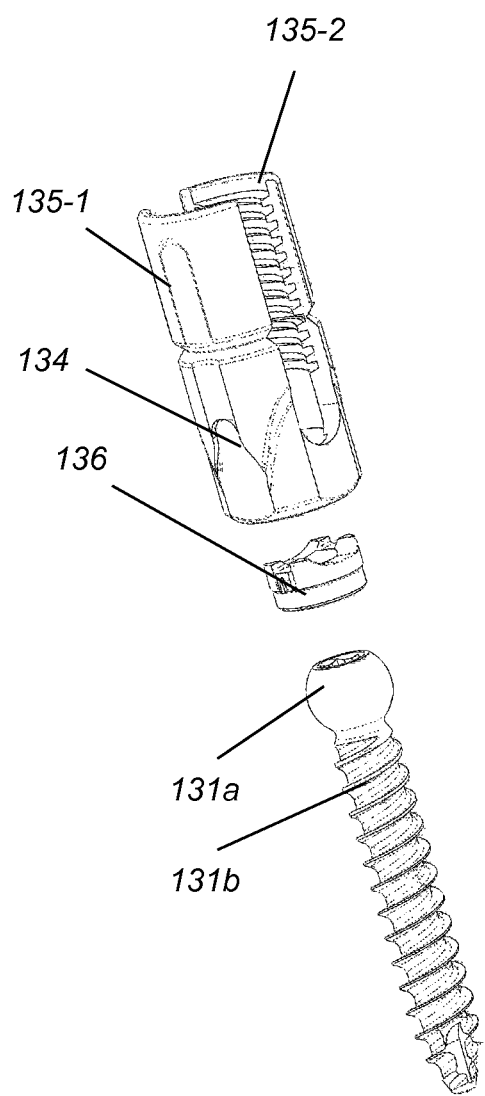
FIG. 25A
FIG. 25B

METHODS, TOOLS AND DEVICES FOR SPINAL FIXATION

CROSS REFERENCE TO RELATED CO-PENDING APPLICATIONS

This application claims the benefit of U.S. provisional application Ser. No. 61/498,668 filed Jun. 20, 2011 and entitled "IMPROVED METHODS, TOOLS AND DEVICES FOR SPINAL FIXATION", the contents of which are expressly incorporated herein by reference.

FIELD OF THE INVENTION

The present invention relates to improved methods, tools and devices for spinal fixation, and more particularly to an improved method for spinal rod insertion.

BACKGROUND OF THE INVENTION

It is well known that traditional surgical procedures in locations deep within a patient's body require a long incision, extensive muscle stripping, prolonged retraction of muscles for visualization, and denervation and devascularization of the adjacent tissue. These procedures result in extensive tissue traumatization and consequently in prolonged recovery time, risk of infections, high hospitalization costs, pain that can be more severe than the pain due to the initial ailment, and in some cases permanent scarring. In minimally invasive surgical procedures, portals are used to access the locations deep in the patient's body. The use of portals rather than a long incision causes less trauma to the adjacent tissue, reduces the recovery time and pain and may be performed in some case under only local anesthesia. The avoidance of general anesthesia reduces post-operative recovery time and the risk of complications.

Minimally invasive surgical procedures are especially desirable for spine surgeries because spine pathologies are located deep within the body without clear muscle planes and there is danger of damaging the adjacent neural and vascular tissues. In treating the majority of spinal pathologies, the spinal muscles are stripped from the bony elements of the spine followed by laminectomy to expose the dura, the nerve roots, and the discs. The incision has to be wide enough and the tissues have to be retracted to maintain a channel from the skin to the floor of the spinal canal that will allow direct visualization.

The destruction to the spinal structures is even more extensive during fusion procedures, which require more lateral tissue dissection and exposure to access the transverse processes and pedicles for placement of pedicle screws, rod constructs for stability, and bone graft under direct vision.

In spine fusion procedures intervertebral spacers or connecting elements, such as rods, plates or wires are placed and fixed between two or more locations of the spine. Placement of these spacers or connecting elements requires open surgery, which is currently one of the major limitations of other percutaneous cannula access methodologies. Accordingly there is a need for improved methods, tools and devices that allow insertion of stabilization rods, screws and wires via minimally invasive spinal surgeries.

SUMMARY OF THE INVENTION

The present invention relates to improved methods, tools and devices for spinal fixation, and more particularly to an improved method for spinal rod insertion.

In general, in one aspect, the invention features a method of fixating two adjacent spinal vertebras via a spinal rod system. The method includes the following steps. First, providing a U-shaped hook tool comprising a hollow tubular U-shaped body having opposite and parallel to each other first and second legs. The first and second legs originate at a common end and terminate into separate open ends. Next, inserting the open end of the first leg into a first location of a first vertebra and pushing the hook tool along an arc-shaped path until the open end of the first leg exits through a second location of an adjacent second vertebra, thereby placing the open end of the first leg above the second vertebra and the open end of the second leg above the first vertebra and the common end in the intervertebral space between the first and second vertebras. Next, providing a spinal stabilization rod comprising first and second ends. Next, providing a folded flexible wire comprising first and second open ends at the front end and a closed loop end at the back end. The closed loop end is attached to the first end of the spinal stabilization rod. Next, inserting the first and second open ends of the folded flexible wire into the open end of the second leg, and threading the folded flexible wire through the tubular U-shaped body and exiting the first and second open ends of the flexible wire through the open end of the first leg. Next, removing the U-shaped tool from the first and second vertebral locations leaving behind the threaded flexible wire and then pulling the first and second open ends of the flexible wire thereby causing the first end of the spinal stabilization rod to be inserted into the first location of the first vertebra, to be pulled through the intervertebral space and to be placed onto the second location of the second vertebra.

Implementations of this aspect of the invention may include one or more of the following features. The method may further include prior to inserting the open end of the first leg of the hook tool into the first location of the first vertebra, inserting guide wires into the first and second locations of the first and second vertebras, respectively, dilating the tissue around the guide wires, forming openings into the first and second locations of the first and second vertebras, and inserting first and second pedicle screws into the first and second locations of the first and second vertebras, respectively. Each of the first and second pedicle screws comprises a threaded screw, a washer and a tulip-shaped seat, wherein the threaded screw comprises an elongated threaded body and a spherical head and wherein the tulip-shaped seat comprises a cylindrical shaped body having a slot and first and second breakable extensions and wherein the threaded screw is configured to pass through an opening formed in the bottom of the tulip-shaped seat while the spherical head is retained within the tulip-shaped seat. The first and second ends of the spinal stabilization rod are placed within the slots of the tulip-shaped seats of the first and second pedicle screws, respectively. The method may further include inserting first and second portals over the first and second pedicle screws. Each portal comprises an inner cannula surrounded by an outer cannula. The inner cannula comprises a threaded top end and a cap configured to be threaded onto the top end after the outer cannula is placed around the inner cannula. The inner and outer cannulas comprise slotted openings. The slotted openings of the first and second portals are arranged inline with each other, thereby forming an elongated slot extending from the first portal to the second portal and the formed elongated slot is shaped and dimensioned to accommodate the spinal stabilization rod. The first end of the spinal stabilization rod comprises a loop and the flexible wire is threaded and secured to the spinal stabilization loop by engaging the spinal stabilization loop with the closed loop end. The method may further include inserting first and second set screws through the first and second portals into the tulip-shaped seats of the first and second pedicle screws and screwing the first and second set screws into the tulip-shaped seats, thereby securing the first and second ends of the spinal stabilization rod into the first and second pedicle screws, respectively. The U-shaped hook tool further includes a handle and a shaft and the distance between the first and second legs is equal to the distance between the first and second adjacent vertebras In general, in another aspect, the invention features a tool assembly for fixating two adjacent spinal vertebras via a spinal rod system. The tool assembly includes a U-shaped hook tool, a spinal stabilization rod, and a folded flexible wire. The U-shaped hook tool includes a hollow tubular U-shaped body having opposite and parallel to each other first and second legs. The first and second legs originate at a common end and terminate into separate open ends. The open end of the first leg is inserted into a first location of a first vertebra and the hook tool is pushed along an arc-shaped path until the open end of the first leg exits through a second location of an adjacent second vertebra, thereby placing the open end of the first leg above the second vertebra and the open end of the second leg above the first vertebra and the common end in the intervertebral space between the first and second vertebras. The spinal stabilization rod has first and second ends and the folded flexible wire has first and second open ends at the front end and a closed loop end at the back end. The closed loop end is attached to the first end of the spinal stabilization rod and the first and second open ends of the flexible wire are inserted into the open end of the second leg, the flexible wire is threaded through the tubular U-shaped body and the first and second open end of the flexible wire exit through the open end of the first leg. The first and second open ends of the flexible wire are pulled thereby causing the first end of the spinal stabilization rod to be inserted into the first location of the first vertebra, to be pulled through the intervertebral space and to be placed onto the second location of the second vertebra.

The details of one or more embodiments of the invention are set forth in the accompanying drawings and description below. Other features, objects, and advantages of the invention will be apparent from the following description of the preferred embodiments, the drawings, and the claims

BRIEF DESCRIPTION OF THE DRAWINGS

Referring to the figures, wherein like numerals represent like parts throughout the several views:

FIG. 25A is a perspective side view of the pedicle screw; and

FIG. 25B is an exploded view of the pedicle screw of FIG. 25A.

DETAILED DESCRIPTION OF THE INVENTION

The present invention relates to improved methods, tools and devices for spinal fixation, and more particularly to an improved method for spinal rod insertion. The improved method for spinal rod insertion includes the following steps.

Figure 1:
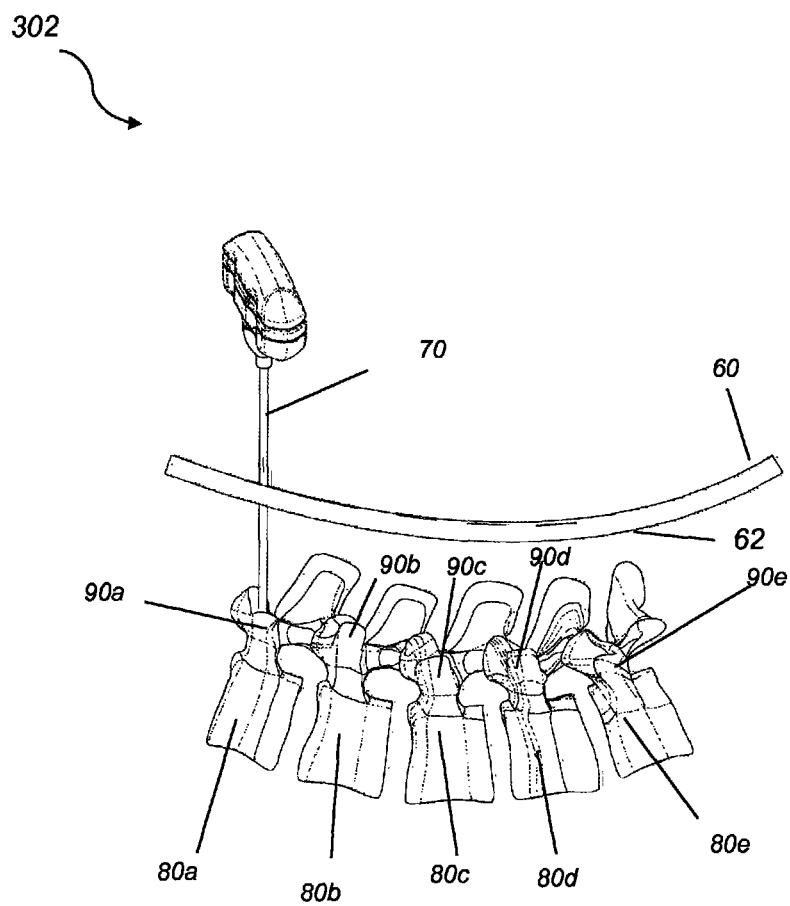
FIG. 1 is a schematic view of the step of inserting a Jamshidi® needle in a pedicle of a first vertebra.
Figure 2:
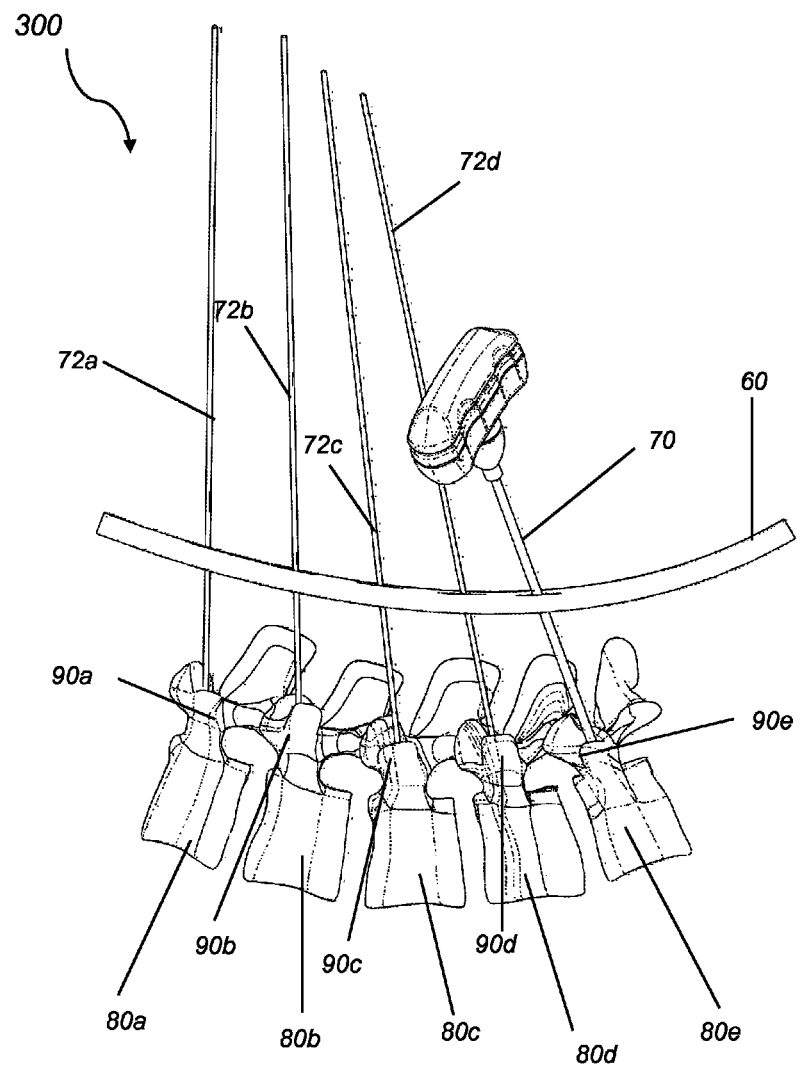
FIG. 2 is a schematic view of the step of inserting guide wires in the pedicle bone openings created with the Jamshidi® needle of FIG. 1.
Figure 3A:
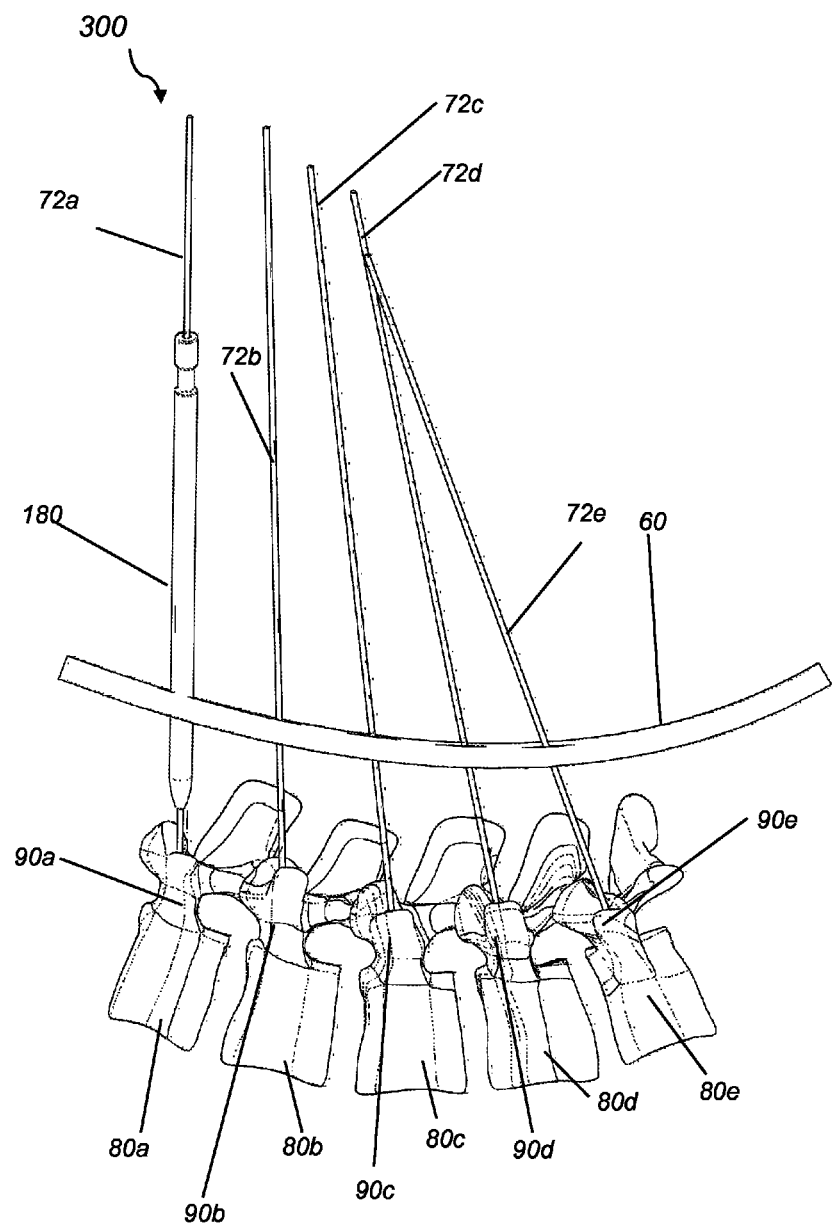
FIG. 3A is a schematic view of the step of inserting a cylindrical dilator.
Figure 3B:
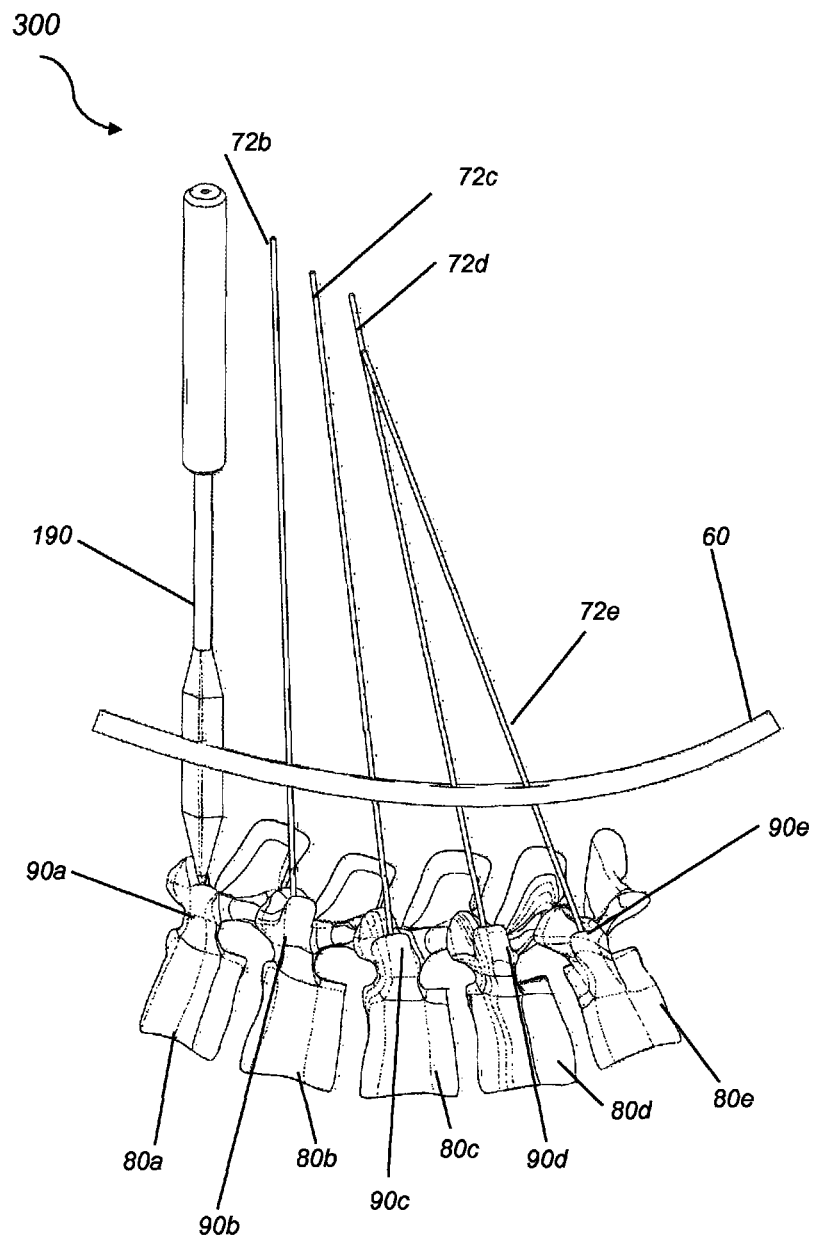
FIG. 3B is a schematic view of the step of inserting a flat blade dilator.
Figure 4:
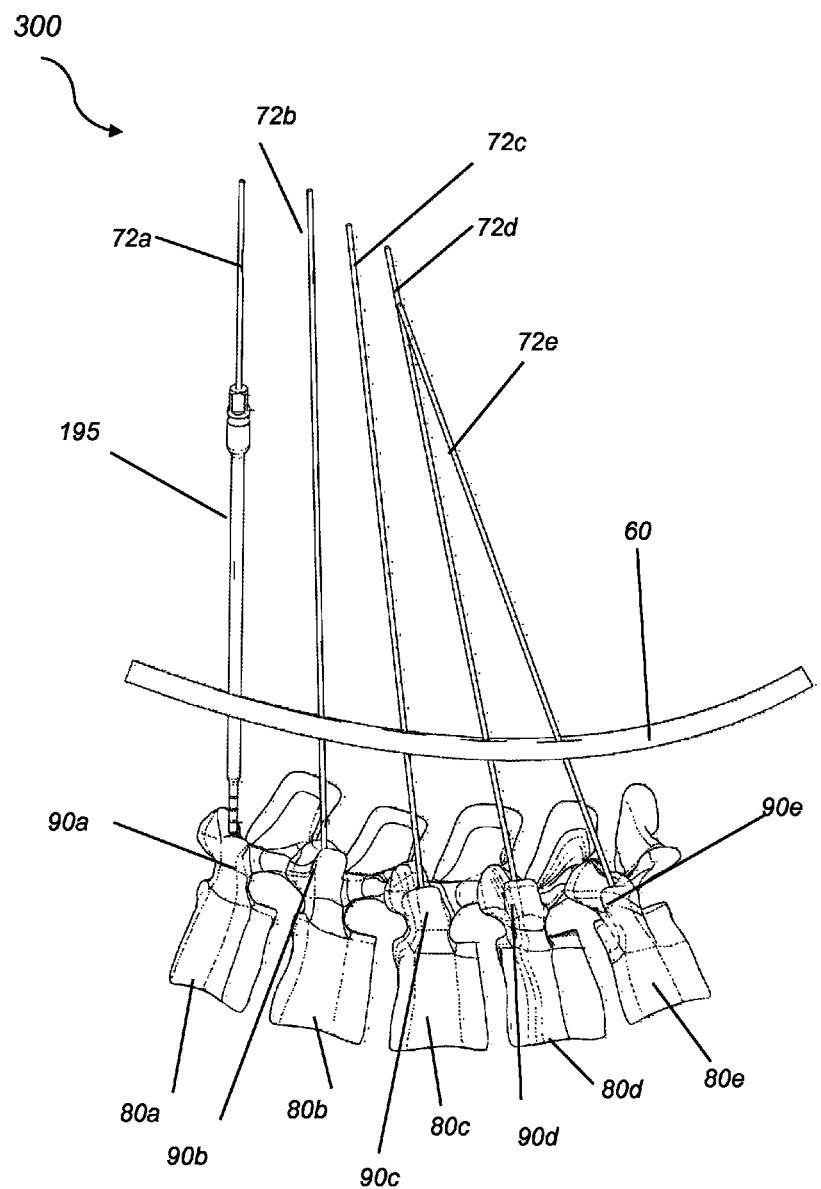
FIG. 4 is a schematic view of the step of taping the openings in the pedicles.
Figure 5:
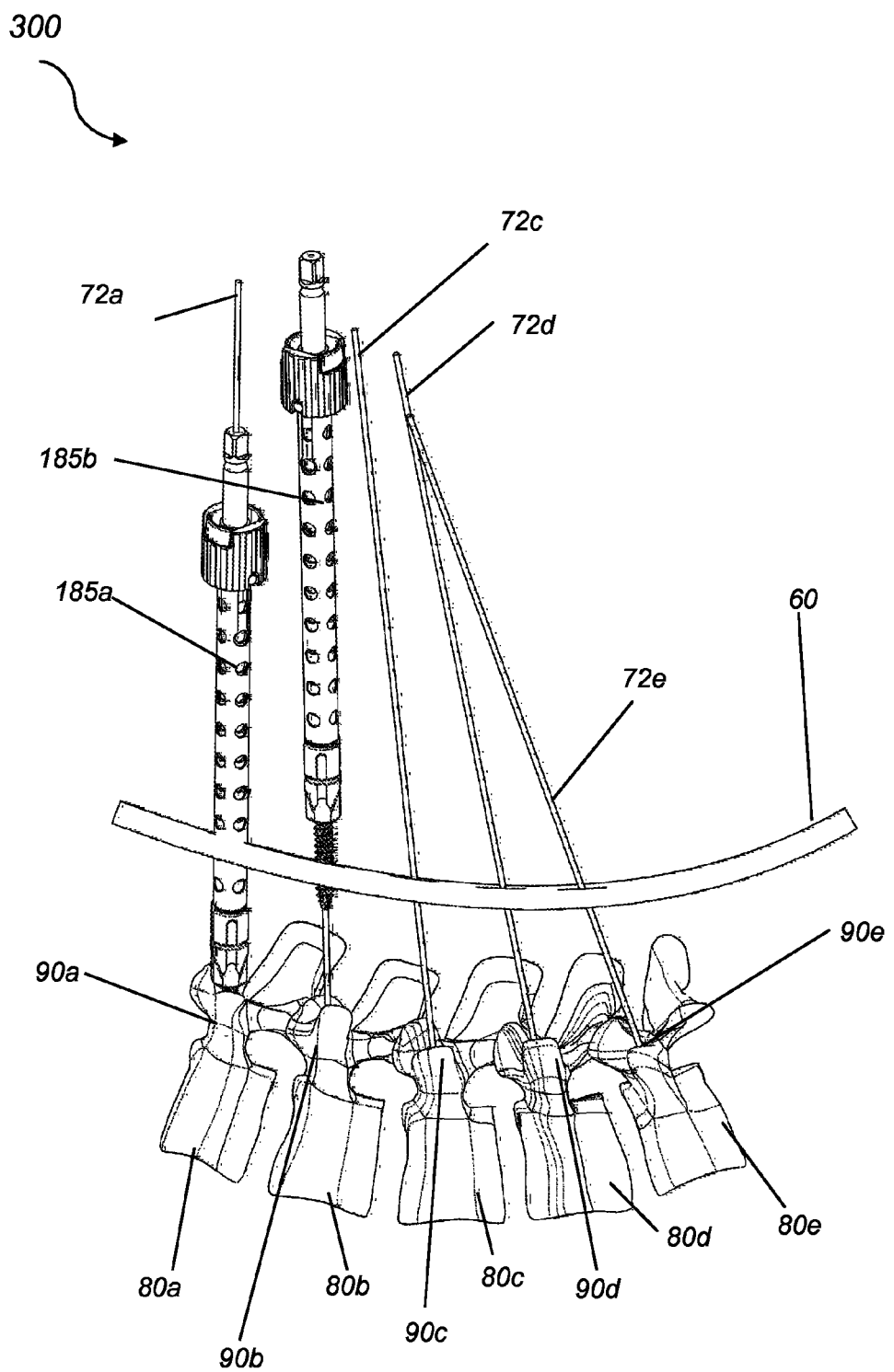
FIG. 5 is a schematic view of the step of inserting pedicle screws in the pedicle openings.
Figure 6:
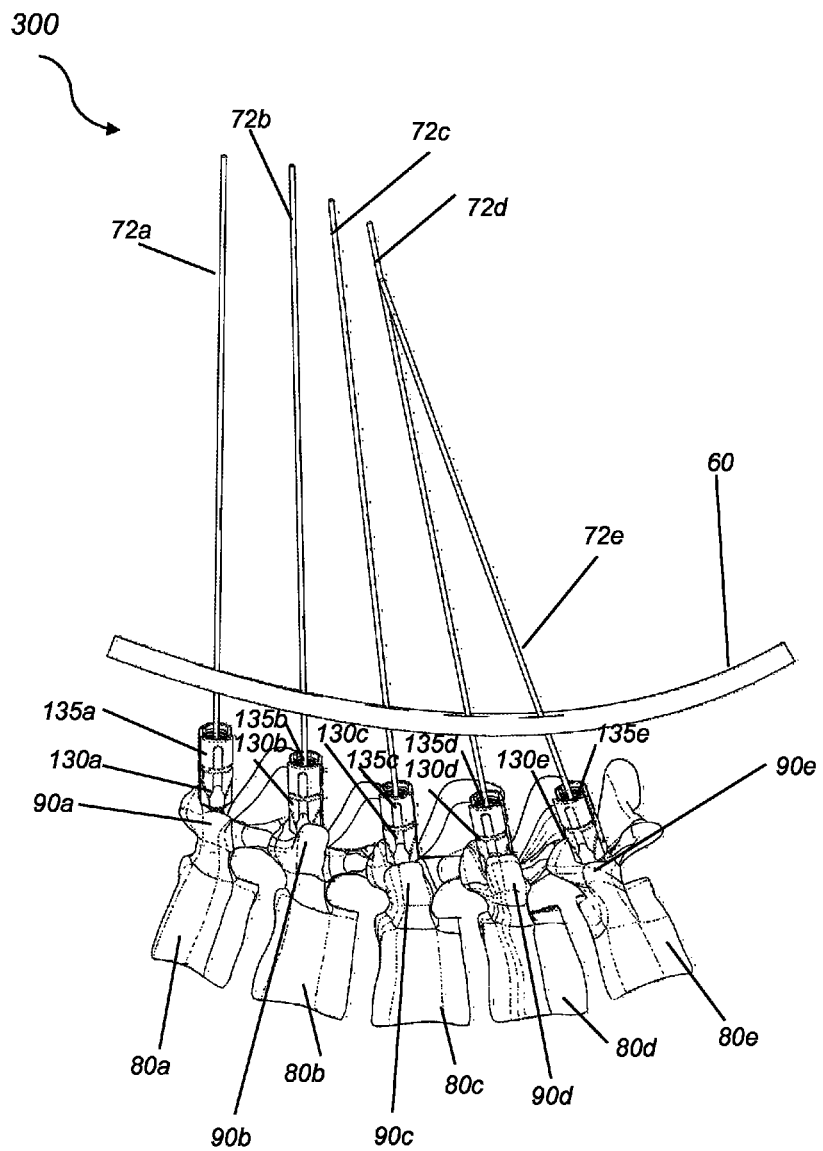
FIG. 6 is a schematic view of the inserted pedicle screws in the pedicles of the adjacent five vertebras.

Referring to FIG. 1, first a Jamshidi® needle 70 is inserted into a pedicle 90a of a first vertebra 80a. The Jamshidi® needle 70 penetrates the outer skin layers 60, the underlying tissue layers 62 and is inserted into pedicles 90a, 90b, 90c, 90d and 90e of adjacent vertebras 80a, 80b, 80c, 80d and 80e, respectively, under radiographic imaging. Next, guide wires 72a, 72b, 72c, 72d and 72e are inserted over the needle 70 in the pedicle locations where the needle was inserted, as shown in FIG. 2. Next, tissue dilators 180 or 190 are used to dilate the tissue around the guide wire locations, as shown in FIG. 3A and FIG. 3B. The tissue dilator may be a cylindrical dilator 180, shown in FIG. 3A or a flat blade dilator 190, shown in FIG. 3B. In either case, the dilator has an elongated central opening extending through its main body and is inserted over the guide wire 72a in each pedicle location. Next, a tapping needle 195 is used to make openings in the pedicle locations 90a-90e, as shown in FIG. 4, and then pedicle screws 130a, 130b, 130c, 130d and 130e are inserted in the openings, as shown in FIG. 5 and FIG. 6. Referring to FIG. 25A and FIG. 25B, pedicle screw 130 includes a threaded screw 132, a washer 136 and a tulip-shaped seat 134. The threaded screw 132 includes a threaded body 131a and a spherical head 131a. The tulip-shaped seat 134 includes a seat 134 having a slot 133 and breakable extensions (or tabs) 135-1 and 135-2 upward extending from its sides. The threaded screw 132 passes through an opening formed in the bottom of the seat 134 and washer 136 is placed inside the seat 134 on top of the spherical head 131a. The upper surface of washer 136 is curved and its curvature is dimensioned to receive a cylindrical stabilization rod, as will be described below.

Figure 7:
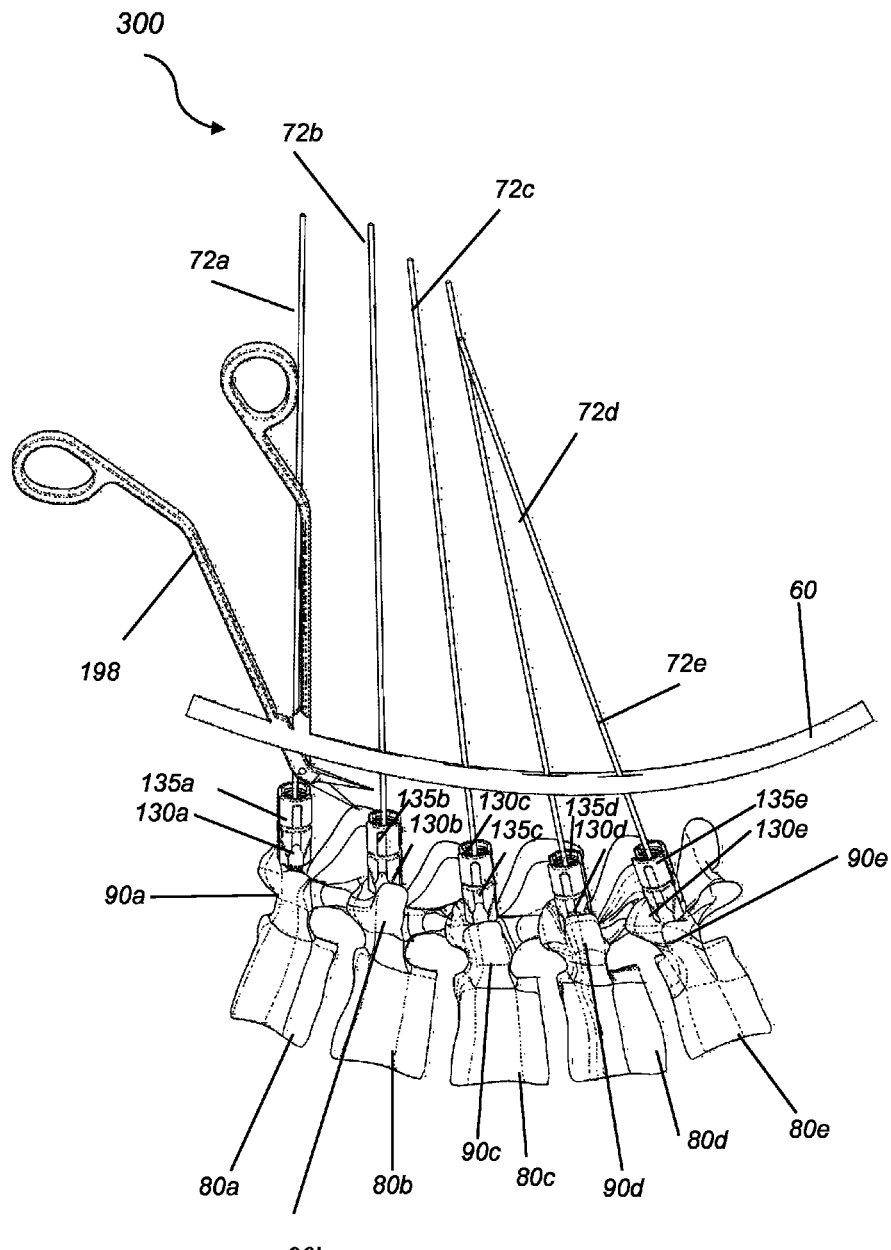
FIG. 7 is a schematic view of the step of cutting the fascia in the areas between the adjacent five vertebras.
Figure 8:
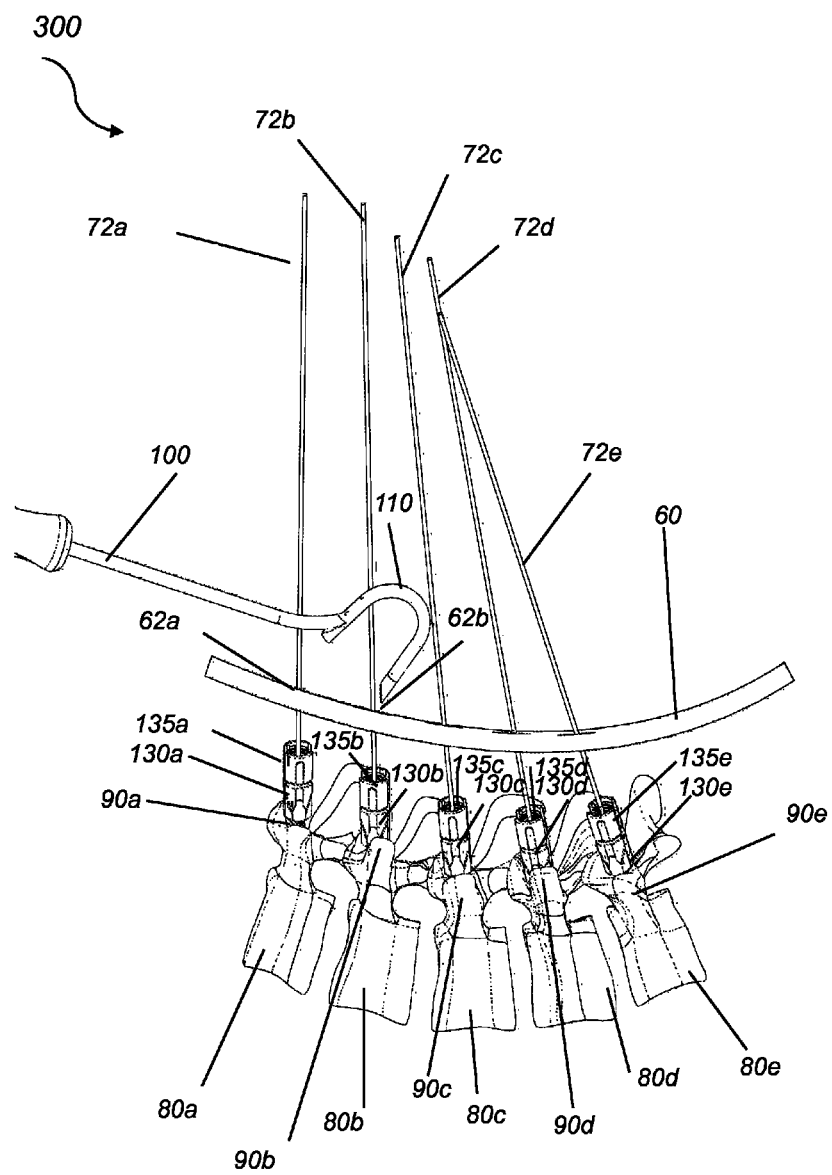
FIG. 8 is a schematic view of the step of inserting a threading hook tool over the first vertebra.
Figure 9:
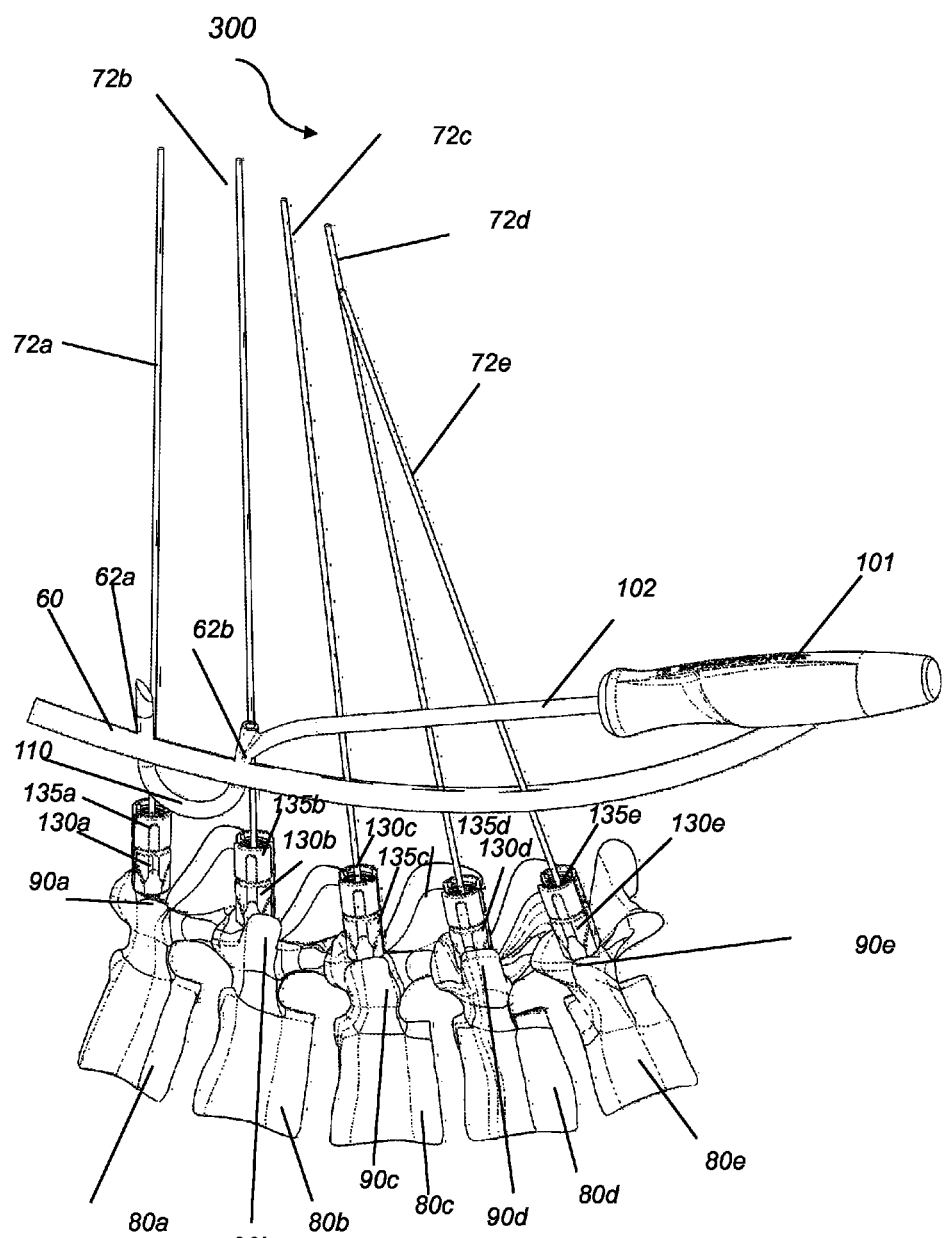
FIG. 9 is a schematic view of the step of engaging the adjacent vertebra with the hook tool of FIG. 8.
Figure 10:
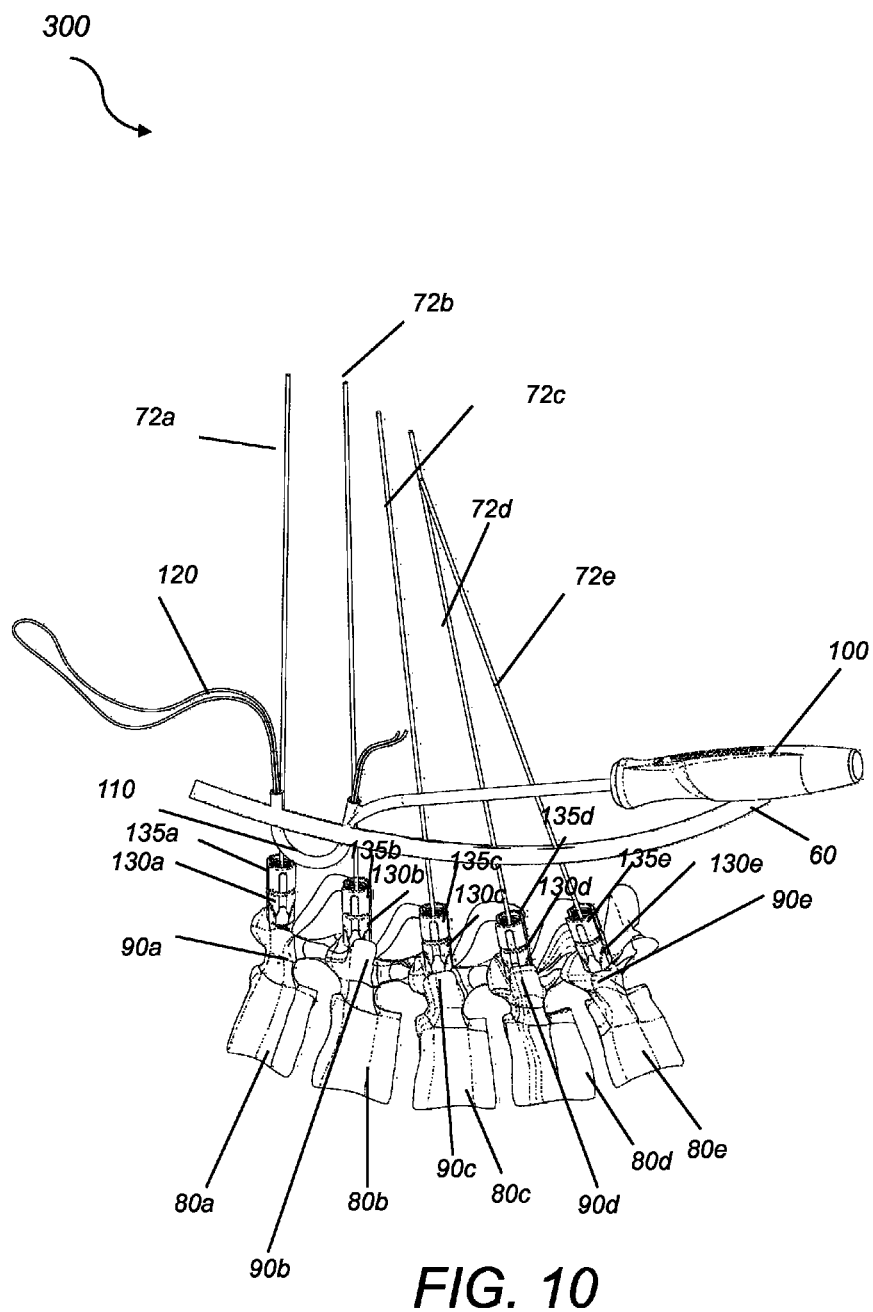
FIG. 10 is a schematic view of the step of threading a flexible wire through the hook tool of FIG. 8.
Figure 11:
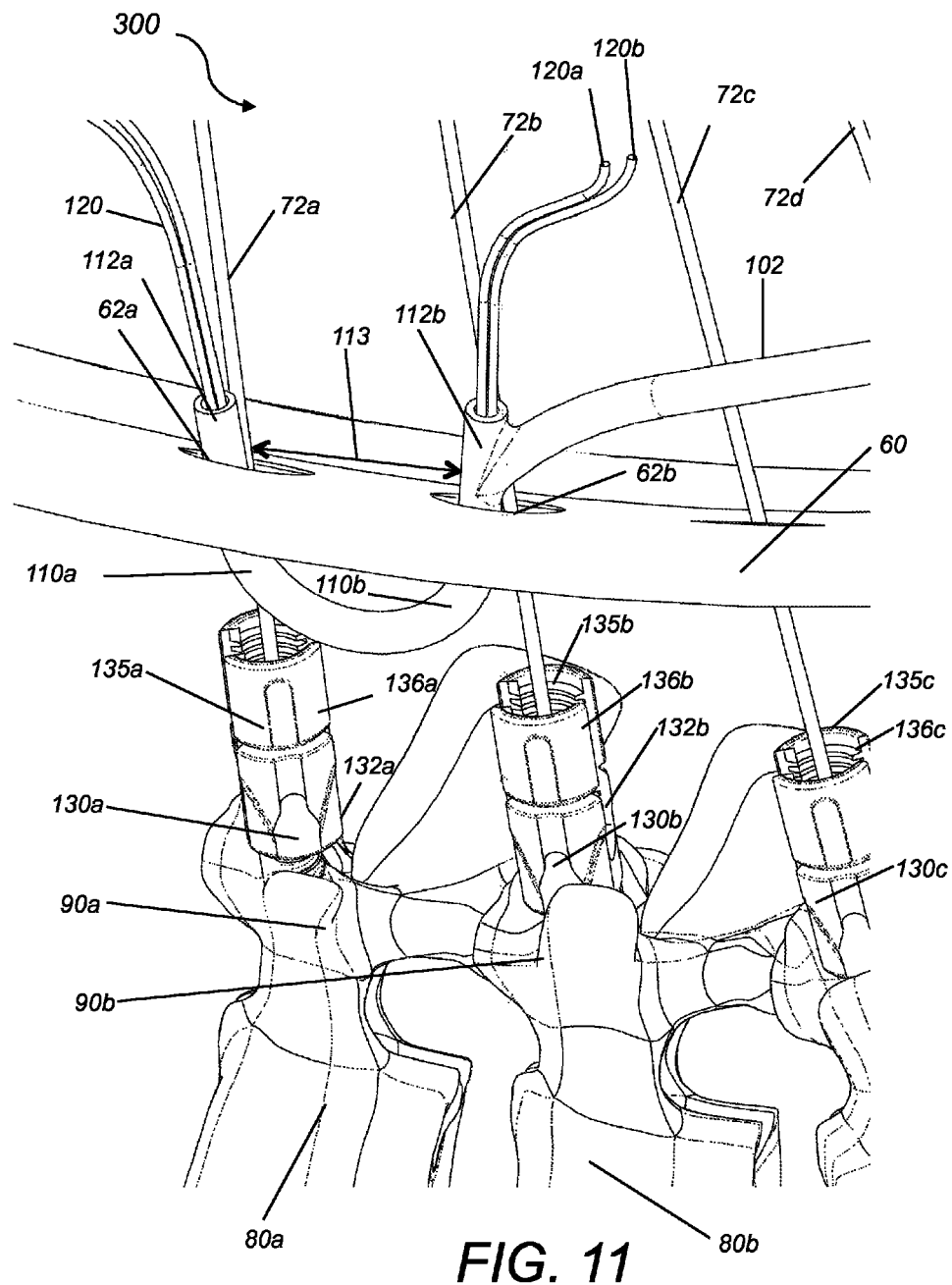
FIG. 11 is a magnified view of area A of FIG. 10.
Figure 12:
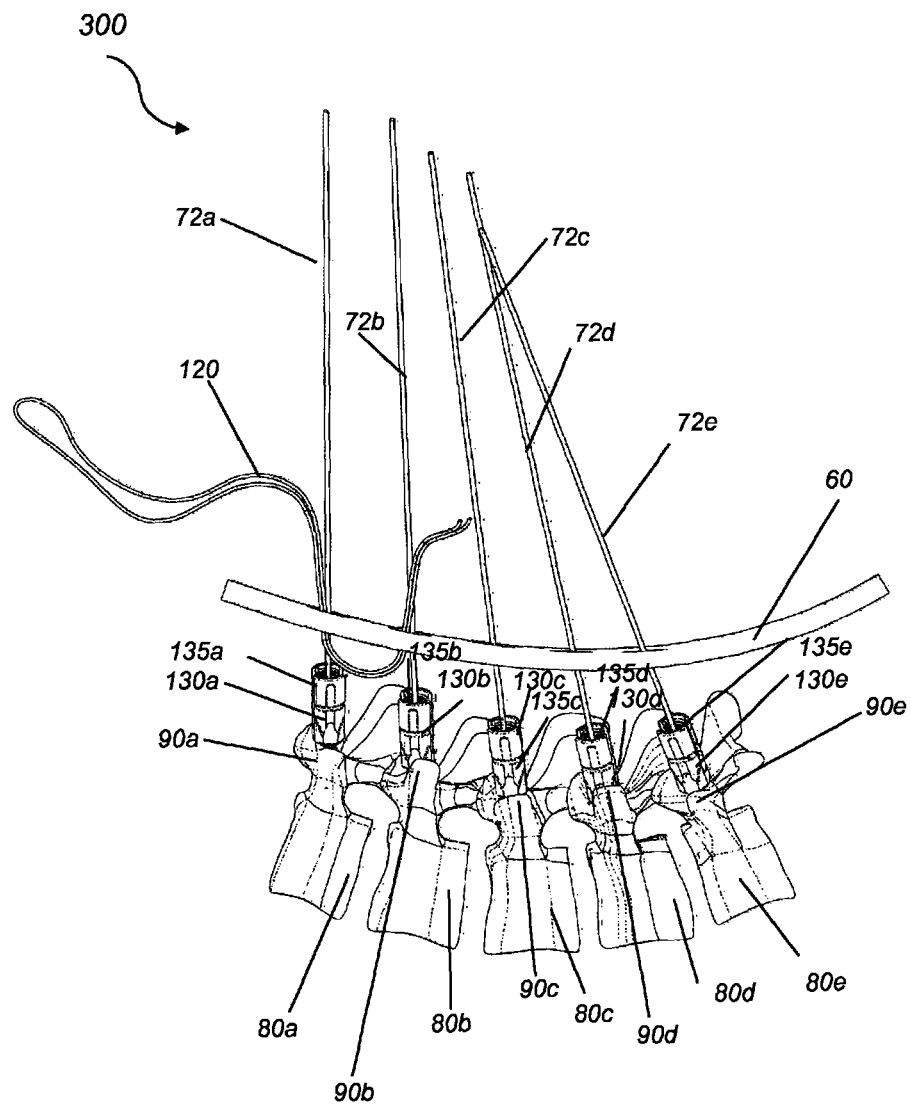
FIG. 12 is a schematic view of the step of removing the hook tool and leaving behind the threaded flexible wire.
Figure 13:
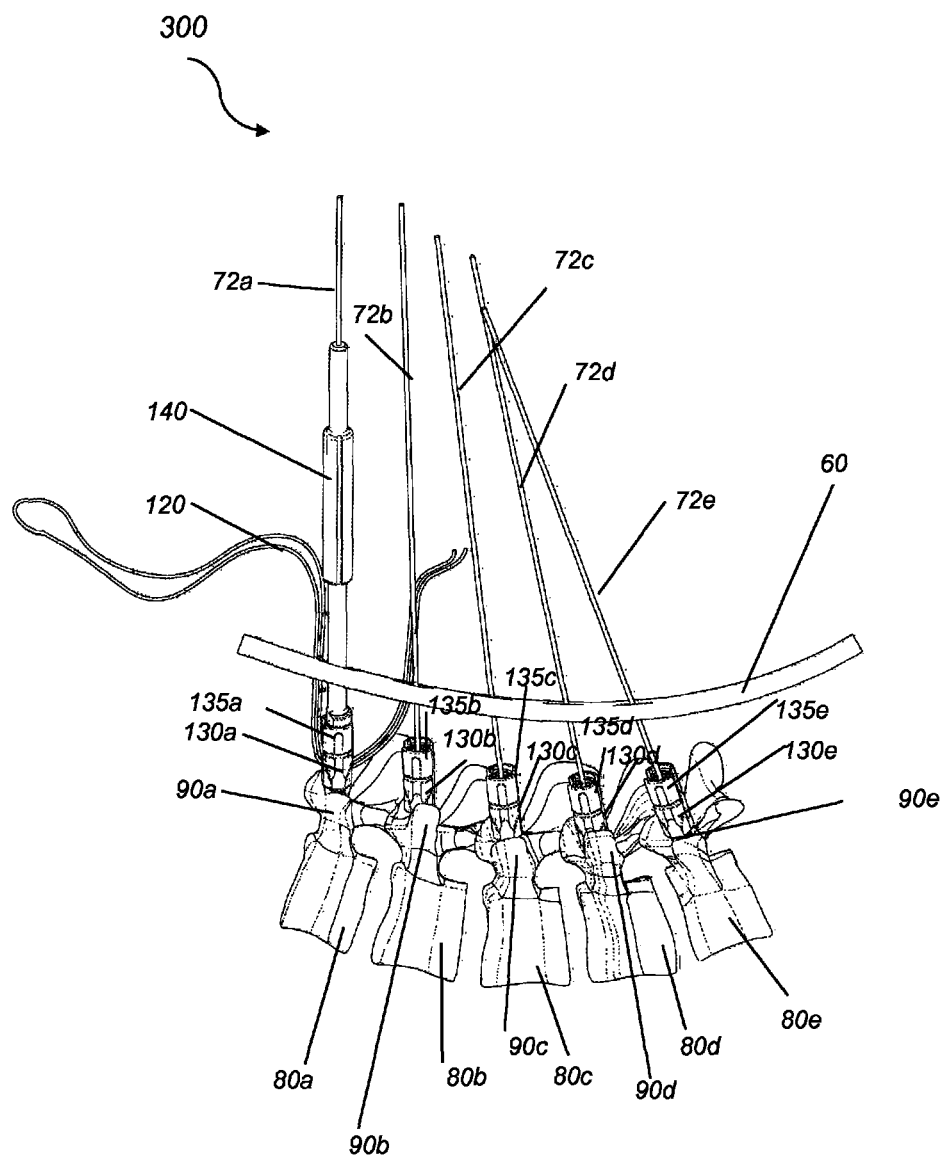
FIG. 13 is a schematic view of the step of inserting a push rod and pushing the flexible wire into the slot of the pedicle screw seat that was mounted in the pedicle of the first vertebra.
Figure 14:
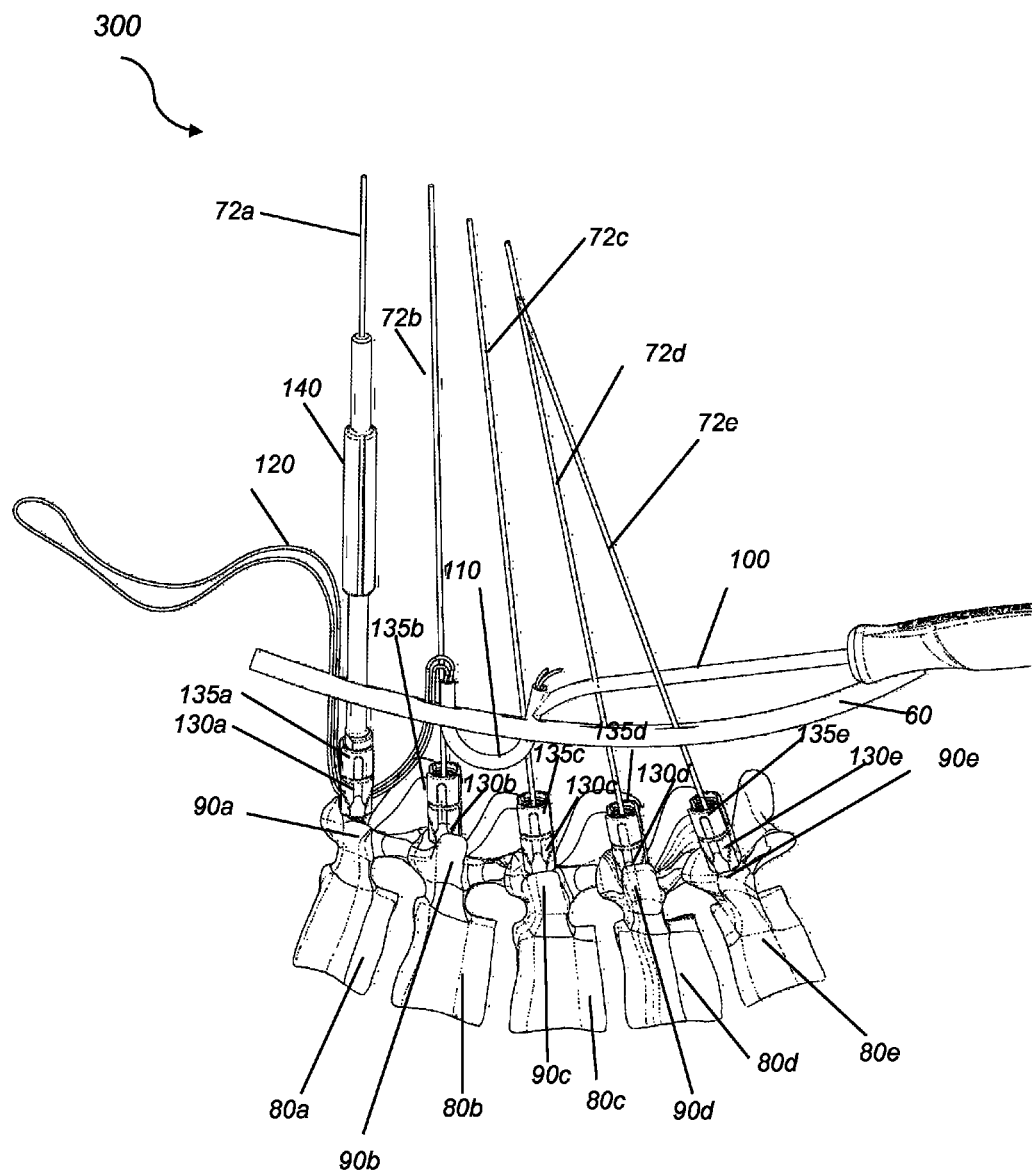
FIG. 14 is a schematic view of the step of inserting the flexible wire through the hook tool in the pedicle of the adjacent vertebra.
Figure 15:
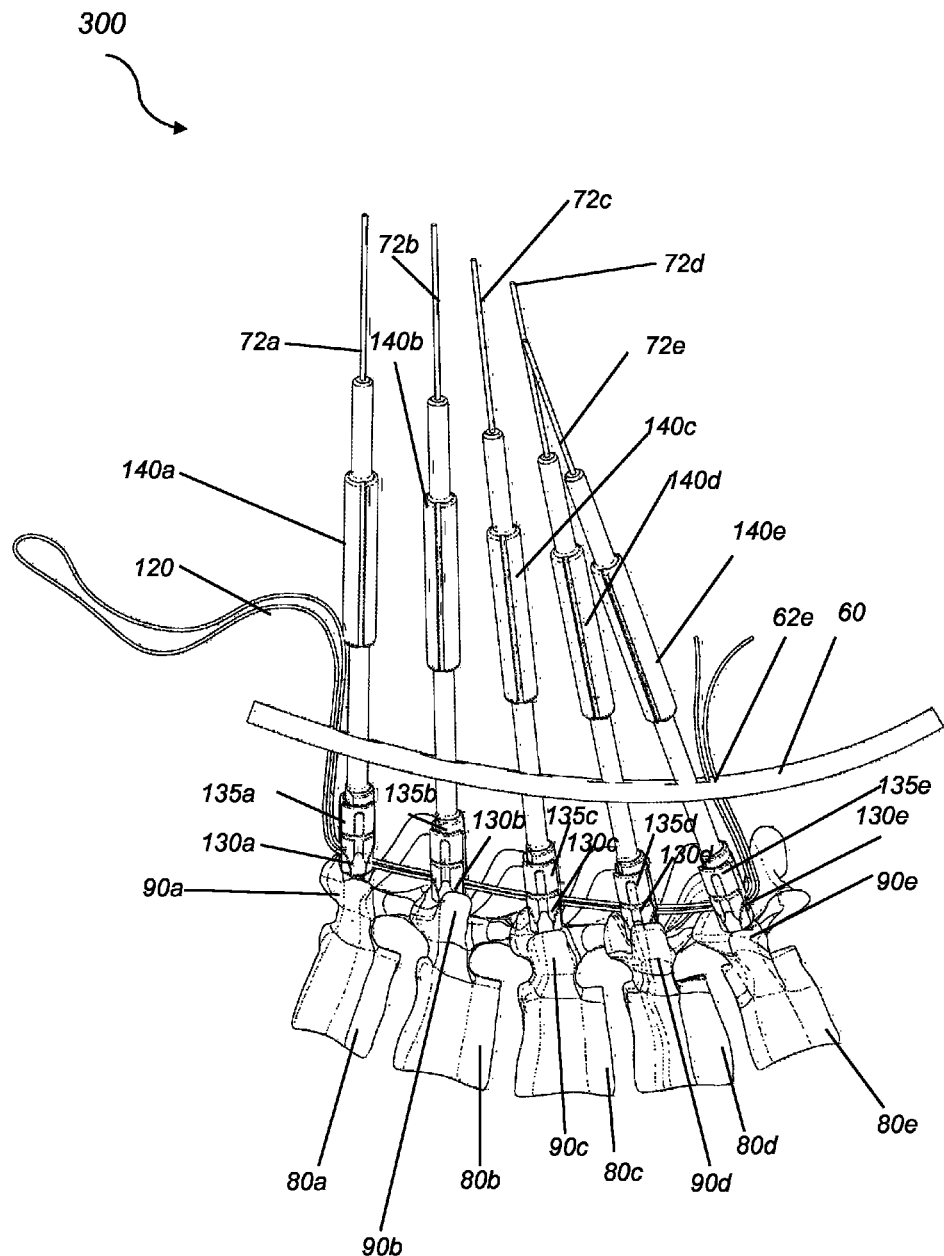
FIG. 15 is a schematic view of the step of inserting push rods and pushing the flexible wire into the slots of the seats of the pedicle screws that were mounted in the pedicles of the adjacent five vertebras.
Figure 17:
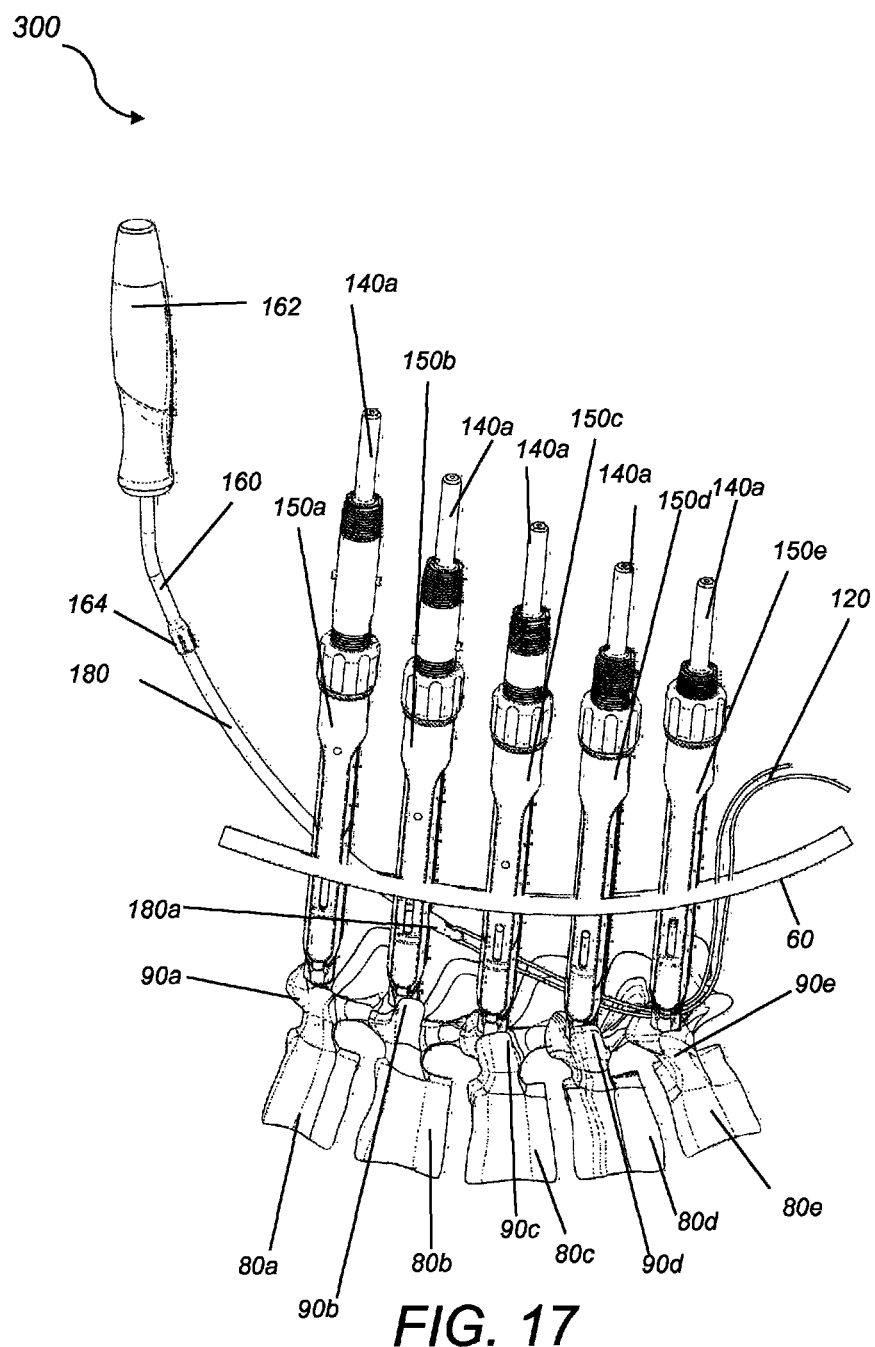
FIG. 17 is a schematic view of the step of inserting the stabilization rod through the portals that were mounted in the pedicles of the adjacent five vertebras.
Figure 17A:
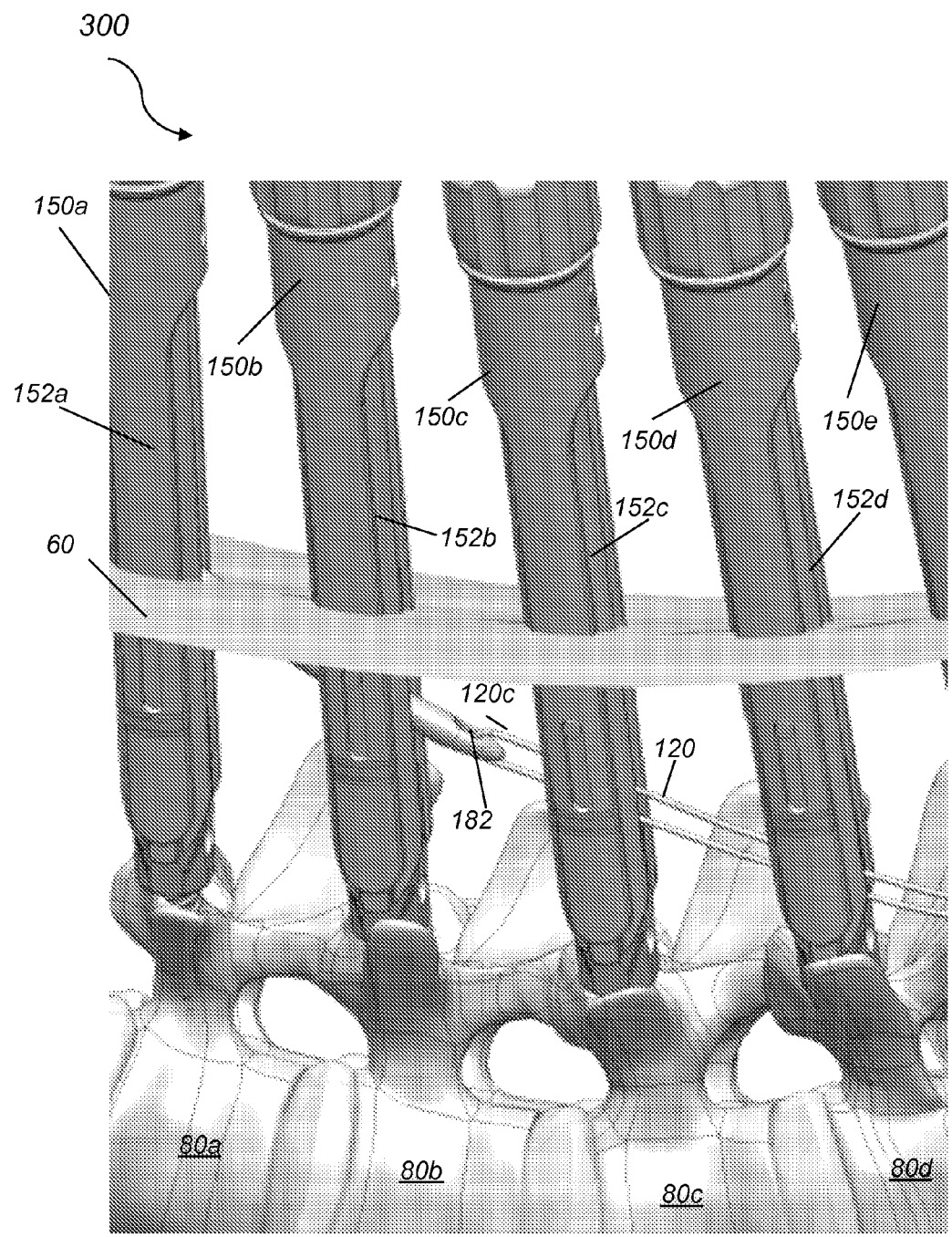
FIG. 17A is a magnified view of area A in FIG. 17.
Figure 18:
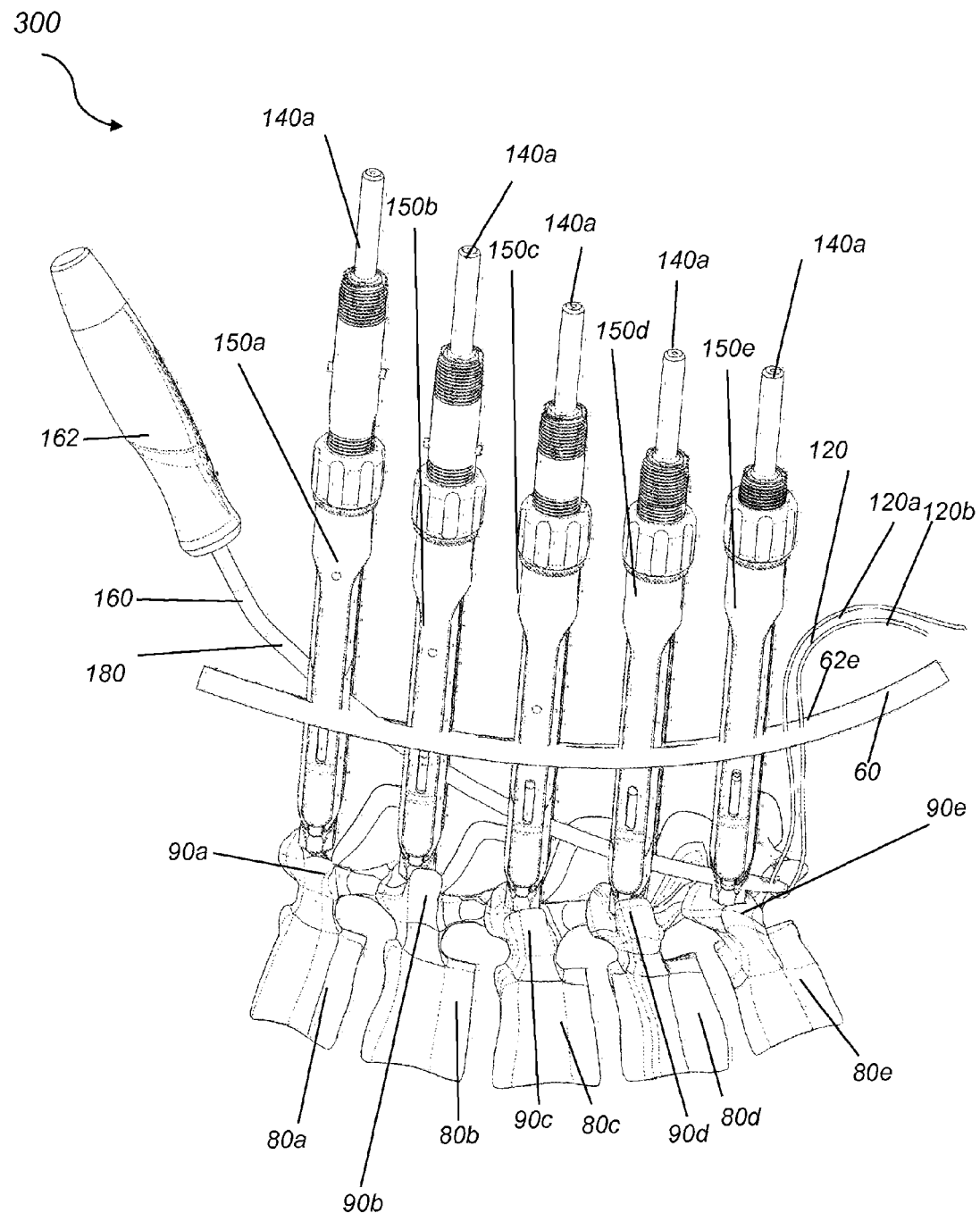
FIG. 18 is a schematic view of the placed stabilization rod through the portals that were mounted in the pedicles of the adjacent five vertebras.

Referring to FIG. 7, in the next step, the fascia between the adjacent vertebras is cut with scissors 198 and then a hook tool 100 is inserted, as shown in FIG. 8. Hook tool 100 includes a handle 101, a shaft 102 and a U-shaped hook end 110 configured to be inserted between two adjacent tissue openings 62a, 62b, as shown in FIG. 9. U-shaped hook end 110 includes two parallel legs 110a, 110b, that are separated from each other by a distance 113, as shown in FIG. 11. U-shaped hook end is formed from a cylindrical hollow tubing and the distance 113 between the two parallel legs 110a, 110b is approximately equal to the distance between two adjacent vertebras. As shown in FIG. 8, leg 110a is inserted into opening 62b and then the hook tool is pushed into the cut fascia between vertebras 80a, 80b and leg 110a exits through adjacent opening 92a. Next, a folded flexible wire 120 is inserted into the U-shaped hook tube end 112a and is threaded through the tube, as shown in FIG. 10. Folded wire 120 has two open ends 120a, 120b on the front and a closed loop end 120c on the back, as shown in FIG. 18 and FIG. 17A. The closed loop end 120c was previously threaded through a loop 182 at the front end 180a of the spinal stabilization rod 180, as shown in FIG. 17 and FIG. 17A. The two front open ends 120a, 120b of the folded wire 120 are pulled through the hollow U-shaped hook tube 110 and exit through the tube end 112b, as shown in FIG. 10 and FIG. 11. Next, the hook tool 100 is removed leaving behind the threaded flexible wire 120, as shown in FIG. 12, and then the wire 120 is pushed with tool 140 into the slot 133 of the tulip-shaped seat 134 of the pedicle screw 130a, as shown in FIG. 13. Next, the process or threading the wire 120 is repeated for the adjacent pedicle screw 130b, as shown in FIG. 14. Finally, wire 120 is threaded through all pedicle screws 130a, 130b, 130c, 130d, 130e and the two open ends 120a, 120b exit through the tissue opening 62e over the last vertebra 80e, as shown in FIG. 15.

Figure 16:
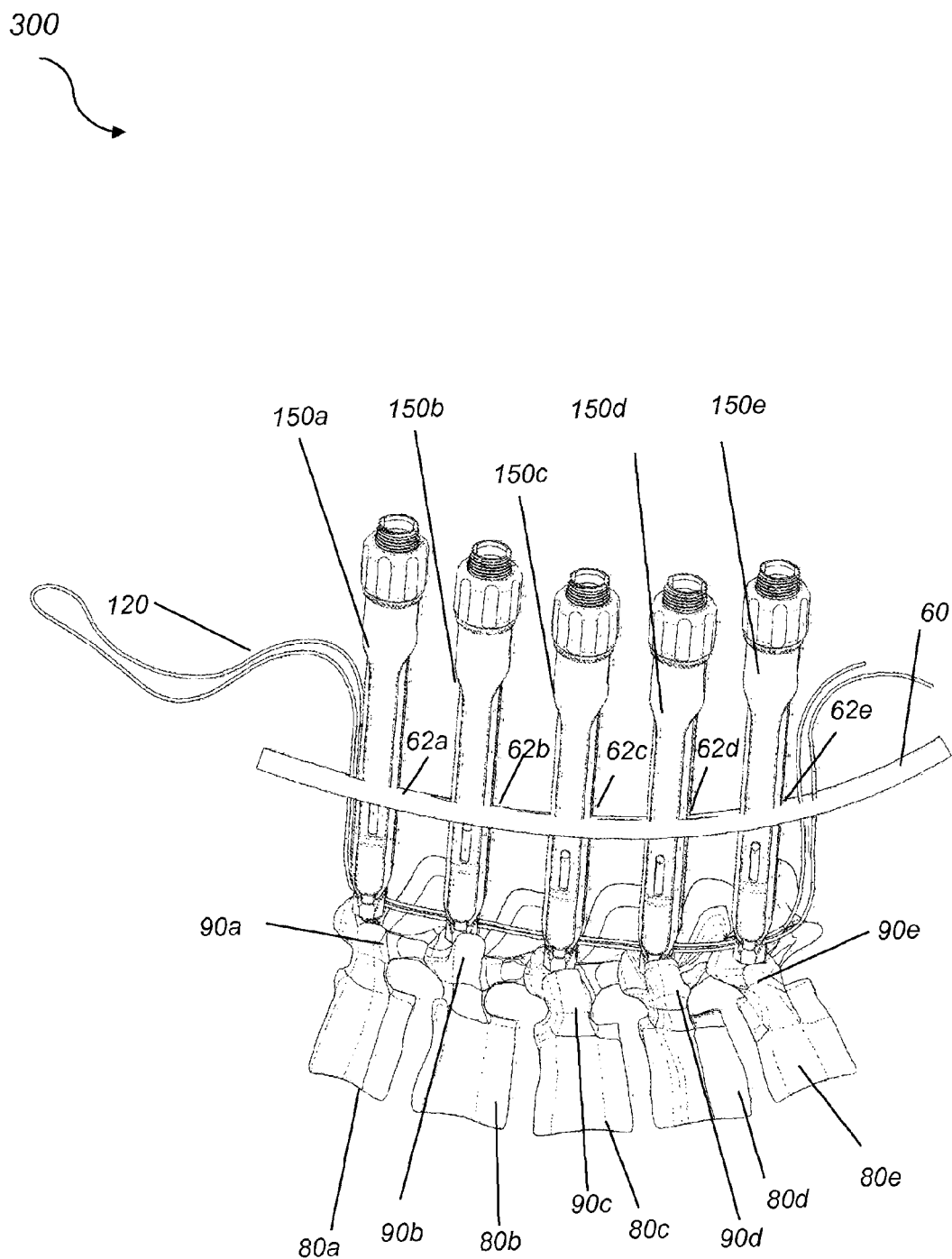
FIG. 16 is a schematic view of the step of inserting portals over the pedicle screws that were mounted in the pedicles of the adjacent five vertebras.
Figure 19:
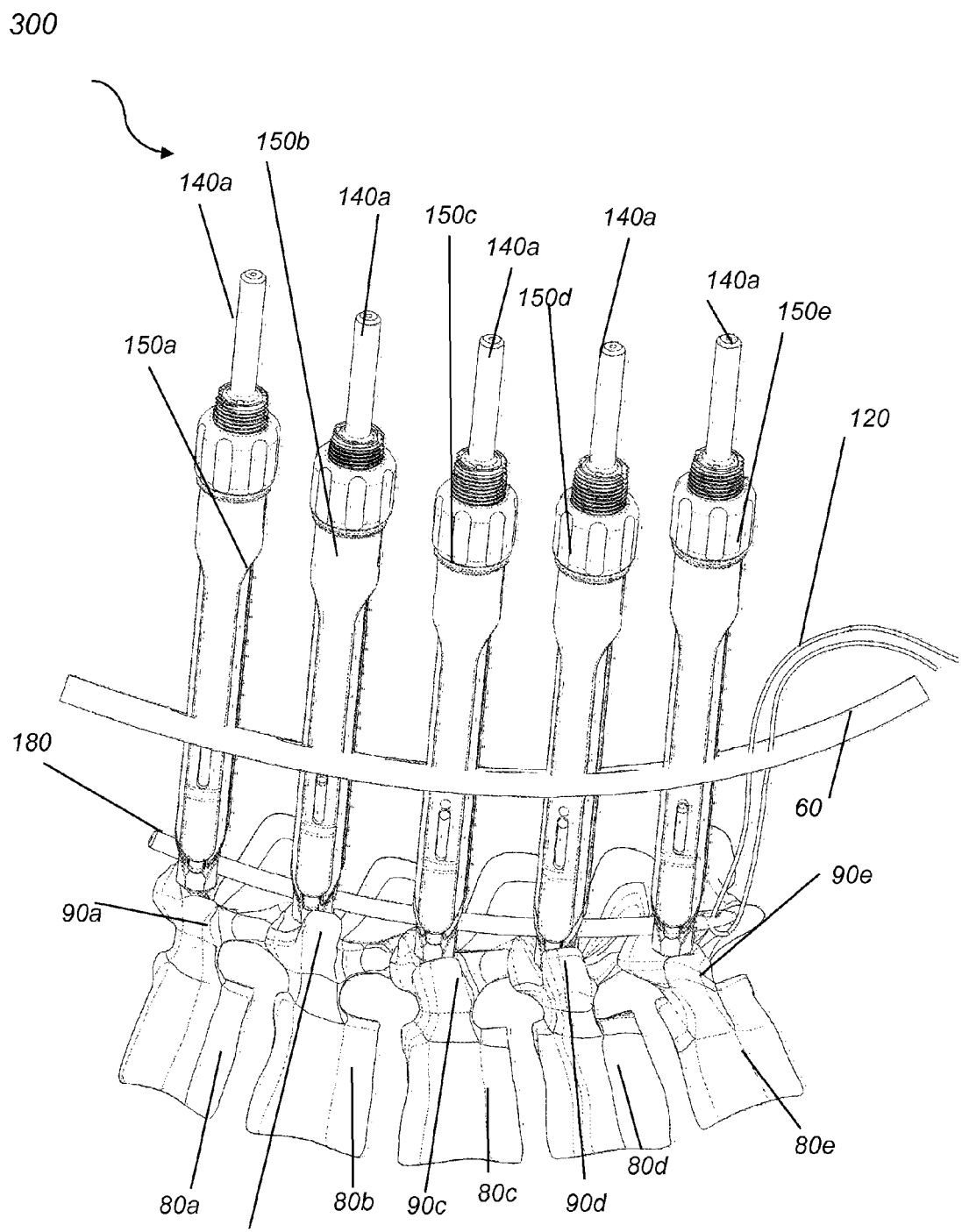
FIG. 19 is a schematic view of the pushed stabilization rod into the seats of the pedicle screws that were mounted in the pedicles of the adjacent five vertebras.
Figure 20:
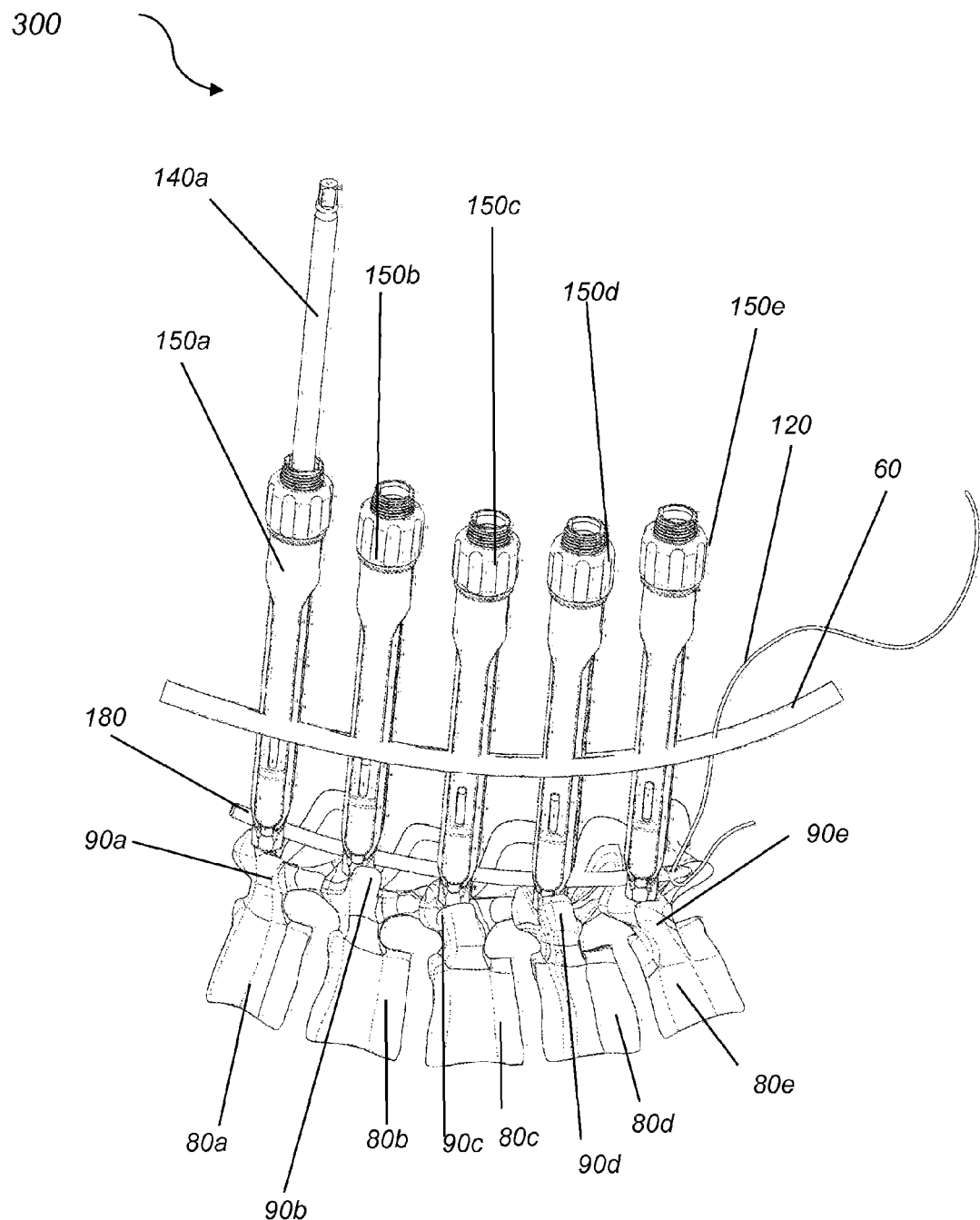
FIG. 20 is a schematic view of the step of securing the stabilization rod with set screws.
Figure 21:
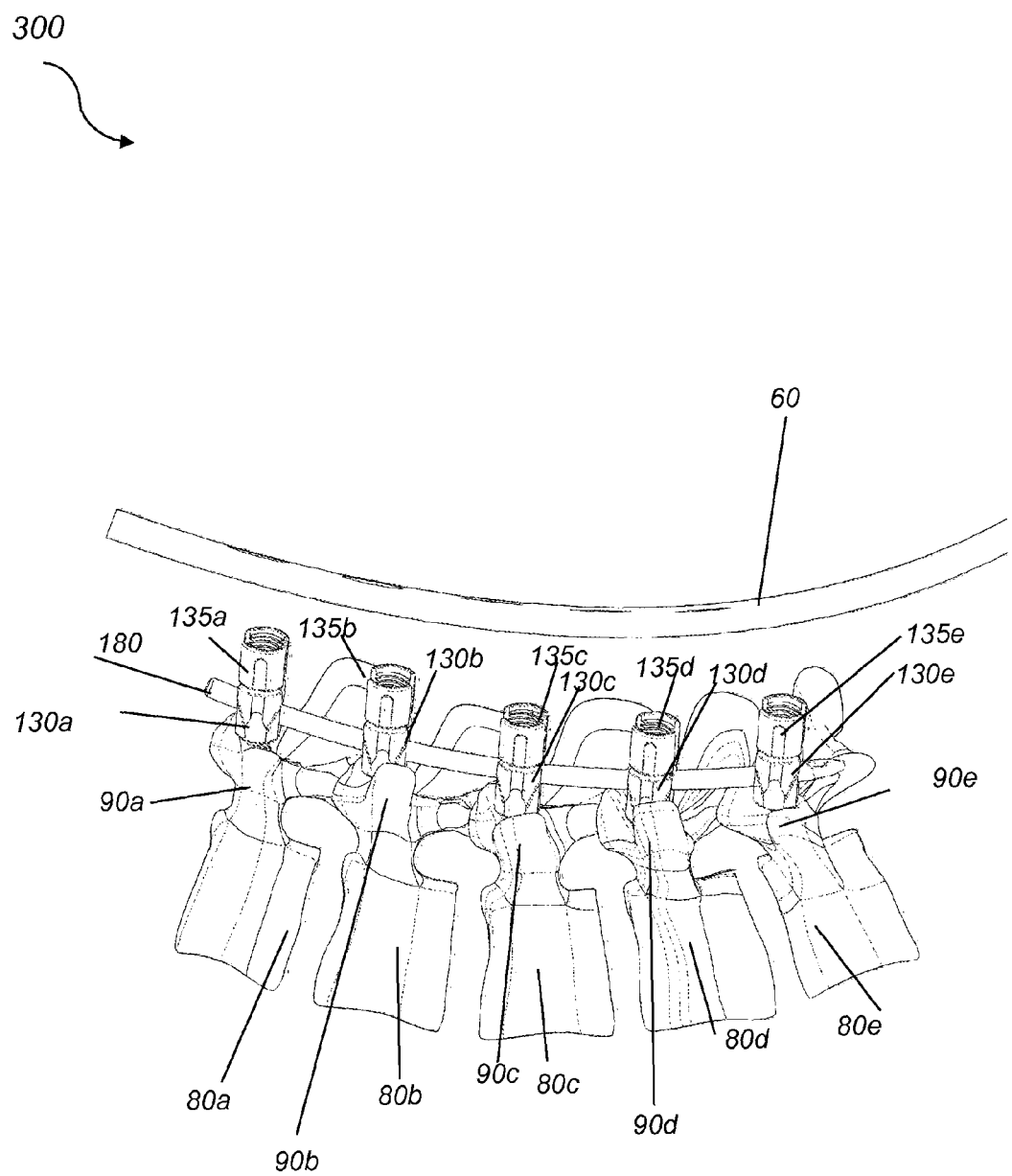
FIG. 21 is a schematic view of the step of removing the portals from the pedicles of the adjacent five vertebras.
Figure 22:
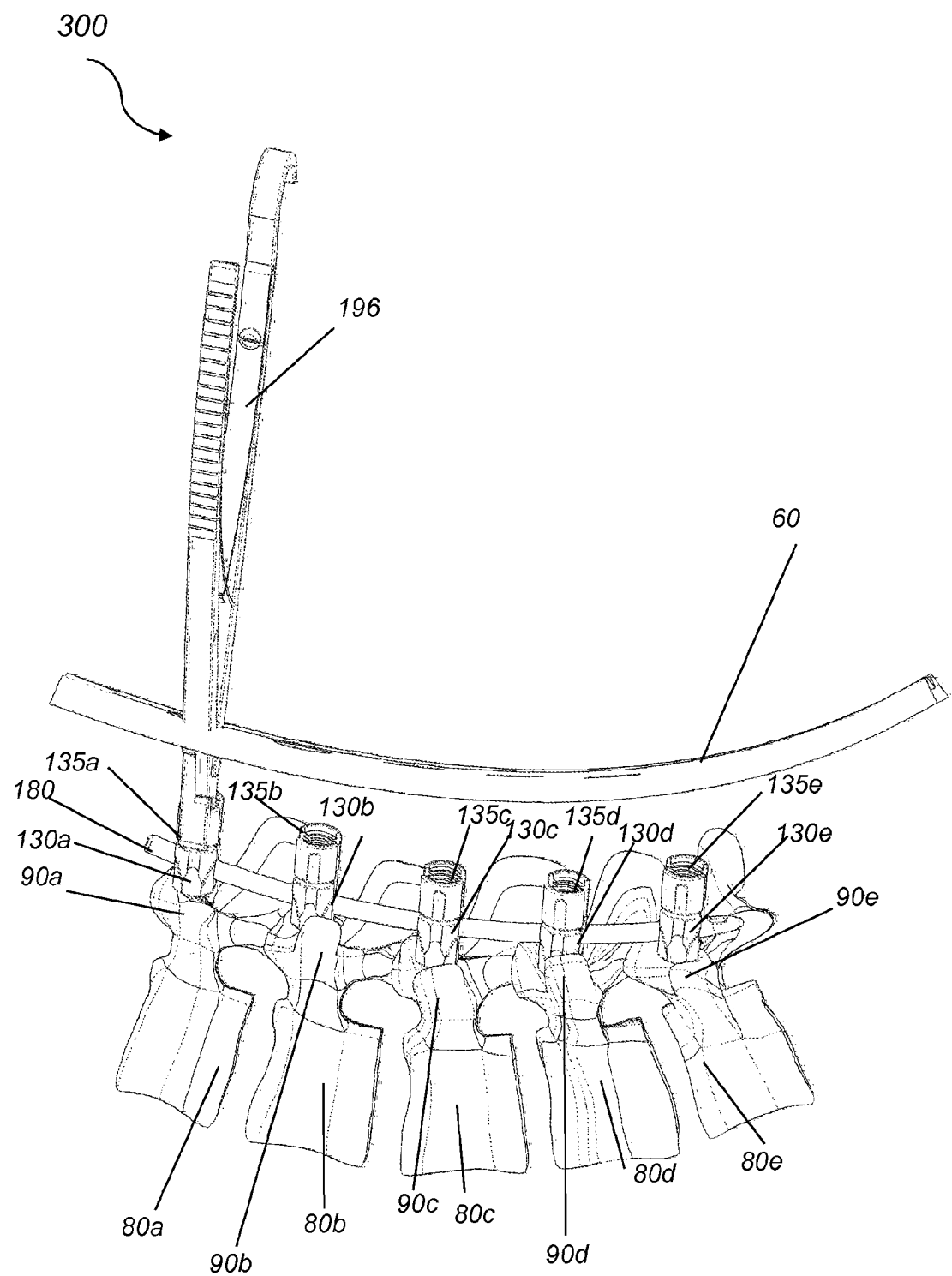
FIG. 22 is a schematic view of the step of breaking the spondi tabs.
Figure 23:
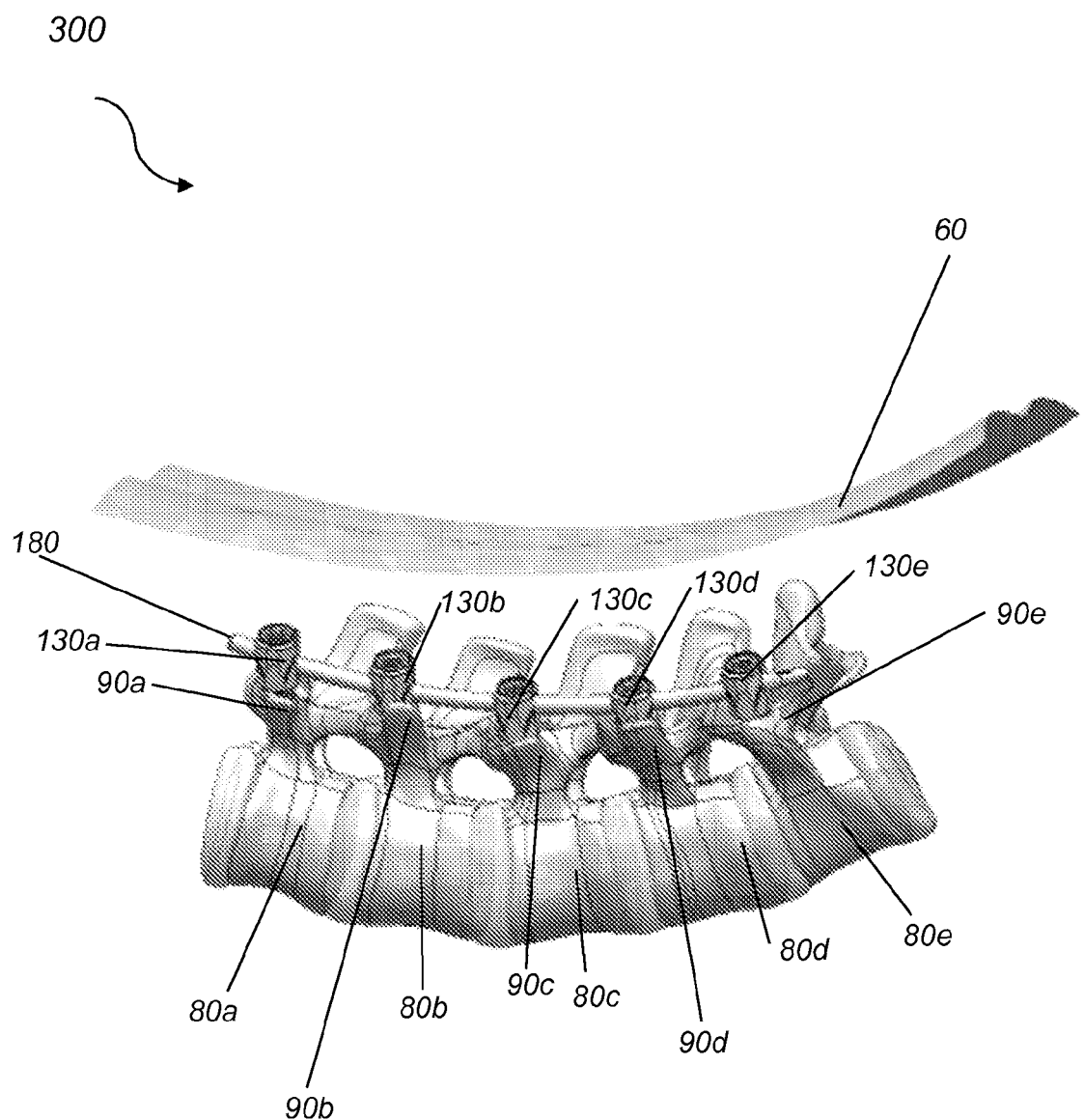
FIG. 23 is a schematic view of the inserted rod and pedicle screw fixation system.
Figure 24:
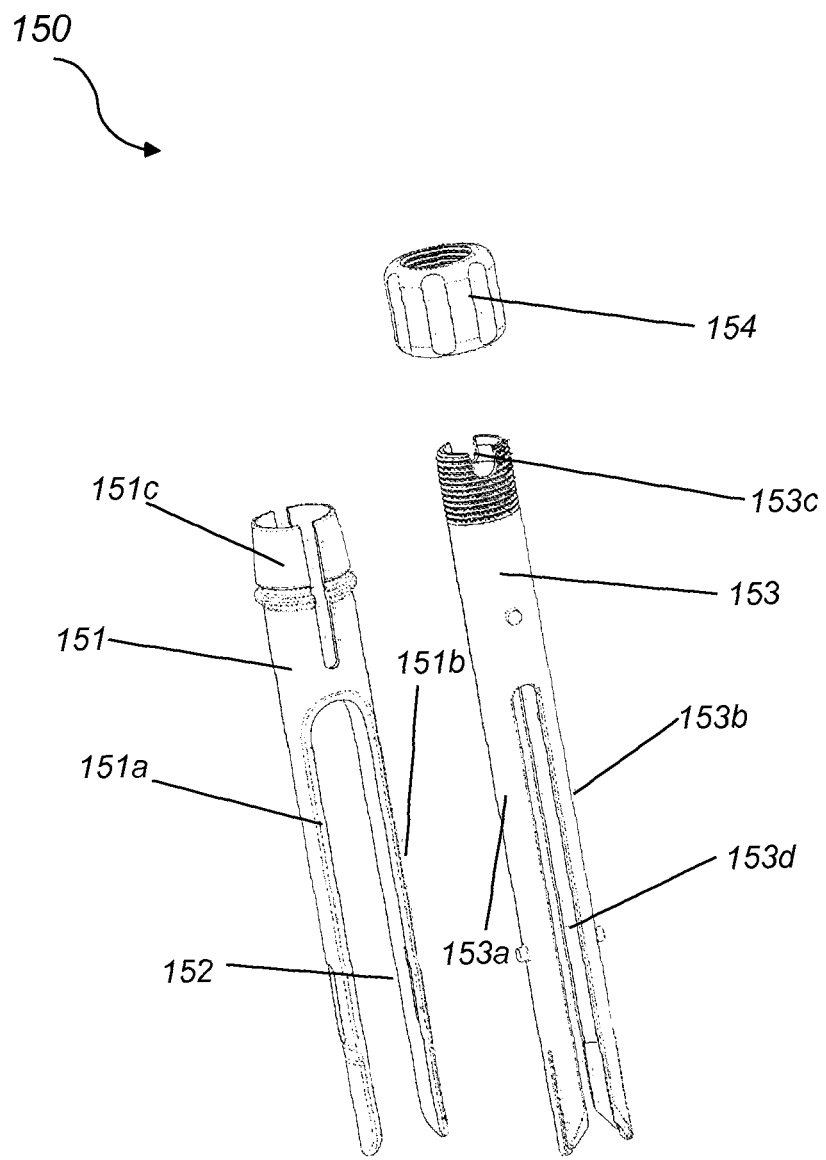
FIG. 24 is a schematic exploded side view of the portal unit.

Referring to FIG. 16, in the next step, portals 150a, 150b, 150c, 150d and 150e are inserted through tissue openings 62a, 62b, 62c, 62d and 62e and are placed over pedicle screws 130a, 130b, 130c, 130d, and 130e, respectively. Referring to FIG. 24, each portal 150 includes an inner cannula 153 surrounded by an outer cannula 151. Inner cannula includes a threaded top end 153c and a cap 154 is threaded onto top end 153c after the outer cannula is placed around it. Both inner and outer cannulas 153, 151 include slotted openings 153d and 152, respectively. Slotted openings 153d, 152 in each portal 150a, 150b, 150c, 150d and 150e are arranged in line with each other and form an elongated slot extending from the first portal 150a to the last portal 150e. Referring to FIG. 17, a stabilizing rod 180 is inserted with a rod push tool 160 through the slotted opening of the first portal 150a into the space over vertebra 80a. The front end 180a of rod 180 includes an opening 182 and wire 120 was previously threaded through the opening 182, as was described above and shown in FIG. 17A. Next, the wire 120 is pulled from the open ends 120a, 120b exiting through tissue opening 62e and in this way the rod 180 is pulled through the slotted openings of the adjacent portals 150b, 150c, 150d and 150e into the space over the adjacent vertebras 80b, 80c, 80d, 80e, respectively, as shown in FIG. 18. Next, the rod 180 is pushed into the slots 133 of the pedicle screws 130a, 130b, 130c, 130d and 130e with tools 140a, 140b, 140c, 140d and 140e, respectively, as shown in FIG. 19. Next, set screws are introduced through the portals 150a, 150b, 150c, 150d and 150e into the seats of the pedicles screws 130a, 130b, 130c, 130d and 130e, respectively, over the stabilization rod 180 and they are screwed into the seats to secure the stabilization rod, as shown in FIG. 20, and then the portals are removed, as shown in FIG. 21. Next, the tabs 135a, 135b, 135c, 135d, 135e are snapped away with tool 196, as shown in FIG. 22, leaving behind the secured stabilization rod 180 and the pedicle screws 130a, 130b, 130c, 130d and 130e, as shown in FIG. 23.

In other embodiments, the stabilization rod 180 is inserted through the slotted openings of portals 150a, 150b, 150c, 150d and 150e into the space over the adjacent vertebras 80a, 80b, 80c, 80d, 80e, prior to the placement of the pedicle screws 130a, 130b, 130c, 130d and 130e in the corresponding pedicle openings.

Several embodiments of the present invention have been described. Nevertheless, it will be understood that various modifications may be made without departing from the spirit and scope of the invention. Accordingly, other embodiments are within the scope of the following claims.

What is claimed is:

1. A method of fixation of two adjacent spinal vertebras via a spinal rod system, comprising:
   providing a U-shaped hook tool comprising a hollow tubular U-shaped body having first and second legs that comprise portions that are opposite and parallel to each other, wherein said first and second legs originate at a common curved portion and terminate into separate open ends;
   inserting the open end of the first leg into a first location of a first vertebra and pushing the hook tool along an arc-shaped path until the open end of the first leg exits through a second location of an adjacent second vertebra;
   providing a spinal stabilization rod comprising first and second ends;
   providing a folded flexible wire comprising first and second open ends at a front end and a closed loop at a back end, wherein the closed loop end is attached to the first end of the spinal stabilization rod;
   inserting first and second open ends of the folded flexible wire into the open end of the second leg, and threading the folded flexible wire through the tubular U-shaped body and exiting the first and second open ends of the flexible wire through the open end of the first leg;
   removing the U-shaped tool from the first and second vertebral locations leaving behind the threaded flexible wire;
   pulling the first and second open ends of the flexible wire thereby causing the first end of the spinal stabilization rod to be inserted into the first location of the first vertebra, to be pulled through the intervertebral space and to be placed onto the second location of the second vertebra.

2. The method of claim 1, further comprising prior to inserting the open end of the first leg of the hook tool into the first location of the first vertebra, inserting guide wires into the first and second locations of the first and second vertebras, respectively, dilating the tissue around the guide wires, forming openings into the first and second locations of the first and second vertebras, and inserting first and second pedicle screws into the first and second locations of the first and second vertebras, respectively.

3. The method of claim 2, wherein each of the first and second pedicle screws comprises a threaded screw, a washer and a tulip-shaped seat, wherein the threaded screw comprises an elongated threaded body and a spherical head and wherein the tulip-shaped seat comprises a cylindrical shaped body having a slot and first and second breakable extensions and wherein the threaded screw is configured to pass through an opening formed in the bottom of the tulip-shaped seat while the spherical head is retained within the tulip-shaped seat.

4. The method of claim 3, wherein the first and second ends of the spinal stabilization rod are placed within the slots of the tulip-shaped seats of the first and second pedicle screws, respectively.

5. The method of claim 4 further comprising inserting first and second portals over the first and second pedicle screws.

6. The method of claim 5, wherein each portal comprises an inner cannula surrounded by an outer cannula and wherein the inner cannula comprises a threaded top end and a cap configured to be threaded onto the top end after the outer cannula is placed around the inner cannula and wherein the inner and outer cannulas comprise slotted openings.

7. The method of claim 6 wherein the slotted openings of the first and second portals are arranged inline with each other, thereby forming an elongated slot extending from the first portal to the second portal and wherein the formed elongated slot is shaped and dimensioned to accommodate the spinal stabilization rod.

8. The method of claim 1, wherein the first end of the spinal stabilization rod comprises a loop and the flexible wire is threaded and secured to the spinal stabilization loop by engaging the spinal stabilization loop with the closed loop end.

9. The method of claim 6, further comprising inserting first and second set screws through the first and second portals into the tulip-shaped seats of the first and second pedicle screws and screwing the first and second set screws into the tulip-shaped seats, thereby securing the first and second ends of the spinal stabilization rod into the first and second pedicle screws, respectively.

10. The method of claim 1, wherein the U-shaped hook tool further comprises a handle and a shaft and wherein the distance between the first and second legs is equal to the distance between the first and second adjacent vertebras.

11. A tool assembly for fixation of two adjacent spinal vertebras via a spinal rod system, comprising:
a U-shaped hook tool comprising a hollow tubular U-shaped body having first and second legs that comprise portions that are opposite and parallel to each other wherein said first and second legs originate at a common curved portion and terminate into separate open ends, wherein the open end of the first leg is configured to be inserted into a first location of a first vertebra and the hook tool is configured to be pushed along an arc-shaped path until the open end of the first leg exits through a second location of an adjacent second vertebra;
a spinal stabilization rod comprising first and second ends;
a folded flexible wire comprising first and second open ends at a front end and a closed loop at a back end, wherein the closed loop end is configured to be attached to the first end of the spinal stabilization rod and wherein the first and second open ends of the flexible wire are configured to be inserted into the open end of the second leg, the flexible wire is configured to be threaded through the tubular U-shaped body and the first and second open end of the flexible wire are configured to exit through the open end of the first leg;
wherein the first and second open ends of the flexible wire are configured to be pulled thereby causing the first end of the spinal stabilization rod to be inserted into the first location of the first vertebra, to be pulled through the intervertebral space and to be placed onto the second location of the second vertebra.

12. The tool assembly of claim 11, further comprising first and second guide wires configured to be inserted into the first and second locations of the first and second vertebras, respectively, a dilator configured to dilate the tissue around the guide wires and to form openings into the first and second locations of the first and second vertebras, and first and second pedicle screws configured to be inserted into the first and second locations of the first and second vertebras, respectively.

13. The tool assembly of claim 12, wherein each of the first and second pedicle screws comprises a threaded screw, a washer and a tulip-shaped seat, wherein the threaded screw comprises an elongated threaded body and a spherical head and wherein the tulip-shaped seat comprises a cylindrical shaped body having a slot and first and second breakable extensions and wherein the threaded screw is configured to pass through an opening formed in the bottom of the tulip-shaped seat while the spherical head is retained within the tulip-shaped seat.

14. The tool assembly of claim 13, wherein the first and second ends of the spinal stabilization rod are configured to be placed within the slots of the tulip-shaped seats of the first and second pedicle screws, respectively.

15. The tool assembly of claim 14, further comprising first and second portals configured to be inserted over the first and second pedicle screws.

16. The tool assembly of claim 15, wherein each portal comprises an inner cannula surrounded by an outer cannula and wherein the inner cannula comprises a threaded top end and a cap configured to be threaded onto the top end after the outer cannula is placed around the inner cannula and wherein the inner and outer cannulas comprise slotted openings.

17. The tool assembly of claim 16, wherein the slotted openings of the first and second portals are arranged inline with each other, thereby forming an elongated slot extending from the first portal to the second portal and wherein the formed elongated slot is shaped and dimensioned to accommodate the spinal stabilization rod.

18. The tool assembly of claim 11, wherein the first end of the spinal stabilization rod comprises a loop and the flexible wire is threaded and secured to the spinal stabilization loop by engaging the spinal stabilization loop with the closed loop end.

19. The tool assembly of claim 15, further comprising first and second set screws configured to be inserted through the first and second portals into the tulip-shaped seats of the first and second pedicle screws and to be screwed into the tulip-shaped seats, thereby securing the first and second ends of the spinal stabilization rod into the first and second pedicle screws, respectively.

20. The tool assembly of claim 11, wherein the U-shaped hook tool further comprises a handle and a shaft and wherein the distance between the first and second legs is equal to the distance between the first and second adjacent vertebras.

* * * * *